(12) United States Patent
Millar

(10) Patent No.: US 7,803,580 B2
(45) Date of Patent: Sep. 28, 2010

(54) AMPLIFICATION BLOCKER COMPRISING INTERCALATING NUCLEIC ACIDS (INA) CONTAINING INTERCALATING PSEUDONUCLEOTIDES (IPN)

(75) Inventor: Douglas Spencer Millar, Revesby (AU)

(73) Assignee: Human Genetic Signatures Pty. Ltd., North Ryde, NSW (AU)

( * ) Notice: Subject to any disclaimer, the term of this patent is extended or adjusted under 35 U.S.C. 154(b) by 568 days.

(21) Appl. No.: 11/575,060

(22) PCT Filed: Sep. 9, 2005

(86) PCT No.: PCT/AU2005/001374

§ 371 (c)(1),
(2), (4) Date: Jan. 9, 2008

(87) PCT Pub. No.: WO2006/026828

PCT Pub. Date: Mar. 16, 2006

(65) Prior Publication Data

US 2009/0130657 A1   May 21, 2009

(30) Foreign Application Priority Data

Sep. 10, 2004   (AU) ............................... 2004905213

(51) Int. Cl.
*C12P 19/34* (2006.01)
*C07H 21/04* (2006.01)

(52) U.S. Cl. ..................................... 435/91.2; 536/24.3

(58) Field of Classification Search .................. None
See application file for complete search history.

(56) References Cited

U.S. PATENT DOCUMENTS

| | | | |
|---|---|---|---|
| 5,629,156 A | 5/1997 | Shah et al. | |
| 5,750,338 A | 5/1998 | Collins et al. | |
| 5,786,146 A | 7/1998 | Herman et al. | |
| 5,824,517 A | 10/1998 | Cleuziat et al. | |
| 5,952,174 A | 9/1999 | Nikiforov et al. | |
| 6,265,171 B1 | 7/2001 | Herman et al. | |
| 6,331,393 B1 | 12/2001 | Laird et al. | |
| 6,692,918 B2 | 2/2004 | Kurn | |
| 6,960,436 B2 | 11/2005 | Cottrell | |
| 7,008,770 B1 | 3/2006 | Berlin | |
| 7,288,373 B2 | 10/2007 | Millar et al. | |
| 7,504,207 B2 | 3/2009 | Bergquist | |
| 2002/0086324 A1 | 7/2002 | Laird et al. | |

(Continued)

FOREIGN PATENT DOCUMENTS

EP   1 130 113   9/2001

(Continued)

OTHER PUBLICATIONS

Cottrell et al. A real-time PCR assay for DNA-methylation using methylation-specific blockers. Nucleic Acids Research 32(1):e10 (8 pages), Jan. 13, 2004.*

(Continued)

*Primary Examiner*—Samuel Woolwine
(74) *Attorney, Agent, or Firm*—Knobbe Martens Olson & Bear LLP

(57) ABSTRACT

An amplification blocker comprising an intercalating nucleic acid (INA) containing two or more internal intercalating pseudonucleotides (IPNs) capable of blocking or reducing nucleic acid amplification. Use of the amplification blocker to block or reduce nucleic acid amplification.

78 Claims, 8 Drawing Sheets

U.S. PATENT DOCUMENTS

| | | | |
|---|---|---|---|
| 2002/0142397 A1 | 10/2002 | Collas et al. | |
| 2003/0073081 A1 | 4/2003 | Mukai et al. | |
| 2003/0082600 A1* | 5/2003 | Olek et al. | 435/6 |
| 2003/0119025 A1 | 6/2003 | Olek et al. | |
| 2003/0143577 A1 | 7/2003 | Hogrefe et al. | |
| 2004/0086944 A1 | 5/2004 | Grigg et al. | |
| 2004/0203004 A1 | 10/2004 | Bernard et al. | |
| 2004/0219539 A1 | 11/2004 | Millar et al. | |
| 2005/0019762 A1 | 1/2005 | Olek | |
| 2005/0059003 A1 | 3/2005 | Enoki et al. | |
| 2005/0118578 A1 | 6/2005 | Mineno et al. | |
| 2005/0202490 A1 | 9/2005 | Makarov | |
| 2006/0014144 A1 | 1/2006 | Christensen et al. | |
| 2006/0051771 A1 | 3/2006 | Murphy et al. | |
| 2006/0166203 A1 | 7/2006 | Took | |
| 2007/0020633 A1 | 1/2007 | Millar | |
| 2007/0026070 A1 | 2/2007 | Vonwiller | |
| 2007/0042365 A1 | 2/2007 | Millar et al. | |
| 2007/0178457 A1 | 8/2007 | Millar | |
| 2007/0178459 A1 | 8/2007 | Millar | |
| 2007/0190530 A1 | 8/2007 | Birkner et al. | |
| 2007/0264653 A1 | 11/2007 | Berlin et al. | |
| 2008/0050738 A1 | 2/2008 | Millar | |
| 2009/0029346 A1 | 1/2009 | Millar et al. | |
| 2009/0042732 A1 | 2/2009 | Millar | |
| 2009/0263909 A1 | 10/2009 | Millar | |

FOREIGN PATENT DOCUMENTS

| | | |
|---|---|---|
| EP | 1 319 718 | 6/2003 |
| WO | WO 98/20157 | 5/1988 |
| WO | WO 95/01456 | 1/1995 |
| WO | WO 95/22623 | 8/1995 |
| WO | WO 97/41254 | 11/1997 |
| WO | WO 97/45559 | 12/1997 |
| WO | WO 98/29108 | 7/1998 |
| WO | WO 99/09211 A2 | 2/1999 |
| WO | WO 99/14226 | 3/1999 |
| WO | WO 99/49081 A2 | 9/1999 |
| WO | WO 00/44934 | 8/2000 |
| WO | WO 00/50869 A2 | 8/2000 |
| WO | WO 01/09374 A2 | 2/2001 |
| WO | WO 01/38565 A2 | 5/2001 |
| WO | WO 01/42493 A2 | 6/2001 |
| WO | WO 01/76451 A2 | 10/2001 |
| WO | WO 02/38801 | 5/2002 |
| WO | WO 02/46452 | 6/2002 |
| WO | WO 02/072880 | 9/2002 |
| WO | WO 02/072880 A | 9/2002 |
| WO | WO 02/097065 | 12/2002 |
| WO | WO 03/008623 A2 | 1/2003 |
| WO | WO 03/048732 | 6/2003 |
| WO | WO 03/051901 A2 | 6/2003 |
| WO | WO 03/052132 A2 | 6/2003 |
| WO | WO 03/052133 A2 | 6/2003 |
| WO | WO 03/052134 A 2 | 6/2003 |
| WO | WO 2004/015139 | 2/2004 |
| WO | WO 2004/065625 | 8/2004 |
| WO | WO 2004/090166 | 10/2004 |
| WO | WO 2004/096825 | 11/2004 |
| WO | WO 2004/111266 A | 12/2004 |
| WO | WO 2005/021778 | 3/2005 |
| WO | WO 2005/056790 A1 | 6/2005 |
| WO | WO 2006/058393 | 6/2006 |
| WO | WO 2006/066353 | 6/2006 |

OTHER PUBLICATIONS

Extended European Search Report issued in corresponding European Application No. 05779000.8, dated Dec. 4, 2008.

Badal Sushma et al.: "The human papillomavirus-18 genome is efficiently targeted by cellular DNA methylation" Virology, vol. 324, No. 2, Jul. 1, 2004, pp. 483-492.

Badal V. et al.: "CpG methylation of human papillomavirus type 16 DNA in cervical cancer cell lines and in clinical specimens: Genomic hypomethylation correlates with carcinogenic progression" Journal Of Virology, The American Society For Microbiology, US, vol. 77, No. 11, Jun. 1, 2003, pp. 6227-6234.

Baleriola C et al.: "Comparison of a novel HPV test with the Hybrid Capture II (hcII) and a reference PCR method shows high specificity and positive predictive value for 13 high-risk human papillomavirus infections" Journal Of Clinical Virology, Elsevier, Amsterdam, NL, vol. 42, No. 1, May 1, 2008, pp. 22-26.

European Search Report issued in corresponding European Application No. 06774977, dated Jul. 28, 2009.

Extended European Search Report issued in corresponding European Application No. 05821631.8, dated Dec. 7, 2008.

Feng et al: "Detection of hypermethylated genes in women with and without cervical neoplasia." Journal of the National Cancer Institute Feb. 16, 2005, vol. 97, No. 4, Feb. 16, 200, pp. 273-282.

Gu W. et al, Depletion of Saccharomyces cerevisiae tRNAHis Guanylyltransferase Thg1p leads to uncharged tRNAH is with additional m5C, Mol Cell Biol. Sep. 2005; vol. 25, No. 18, pp. 8191-8201.

International Search Report issued on corresponding PCT Application No. PCT/AU2006/000755, dated Aug. 30, 2006.

International Search Report issued on corresponding PCT Application No. PCT/AU2008/000367, dated May 14, 2008.

Kalantari, Mina et al. "Conserved methylation patterns of human papillomavirus type 16 DNA in asymptomatic infection and cervical neoplasia," Journal of Virology, vol. 78, No. 23, Dec. 2004, pp. 12762-12772.

Kim T Y et al: "DNA hypermethylation in gastric cancer" Alimentary Pharmacology & Therapeutics, vol. 20, No. Suppl. 1, Jul. 2004, pp. 131-142.

Kozak et al.: "Influence of secondary structure on binding and migration of 40S ribosomal subunits," Cell, vol. 19, 1980, pp. 79-90.

Malyukova A V et al: "Methylation of the Putative Tumor Suppressor Gene RASSF1A in Primary Cervical Tumors" Molecular Biology, Kluwer Academic Publishers-Plenum Publishers, NE, vol. 38, No. 6, Nov. 1, 2004, pp. 857-864.

Narayan, Gopeshwar et al: "Frequent Promoter Methylation of CDH1, DAPK, RARB, and HIC1 Genes in Carcinoma of Cervix Uteri: Its Relationship to Clinical Outcome" Molecular Cancer, Biomed Central, London, GB, vol. 2, No. 1, May 13, 2003, p. 24.

Nousbaum, J. et al., "Prospective Characteristics of Full-Length Hepatitis C Virus NS5A Quasispecies during Induction and Combination Antiviral Therapy," Journal of Virology, 74, No. 19, pp. 9028-9038 (2000).

Office Action in U.S. Appl. No. 10/543,017 dated Dec. 8, 2008.
Office Action in U.S. Appl. No. 10/543,017 dated Jun. 20, 2008.
Office Action in U.S. Appl. No. 10/543,017 dated Oct. 19, 2007.
Office Action in U.S. Appl. No. 11/573,873 dated May 4, 2009.
Office Action in U.S. Appl. No. 11/573,873 dated Sep. 2, 2009.
Office Action in U.S. Appl. No. 11/660,586 dated Sep. 15, 2009.

Ratushna V.G. et al.: "Secondary structure in the target as a confounding factor in synthetic oligomer microarray design," BMC Genomics, vol. 6, No. 1, Mar. 2005, p. 31.

Supplementary European Search Report issued on corresponding European Patent Application No. EP 05 81 3335, dated Mar. 12, 2009.

Supplementary European Search Report issued on corresponding European Patent Application No. EP 06 77 4977, dated Jul. 28, 2009.

Ushijima Toshikazu et al: "Aberrant methylations in cancer cells: Where do they come from?" Cancer Science, vol. 96, No. 4, Apr. 2005, pp. 206-211.

Verma M: "Viral Genes and Methylation" Annals of the New York Academy of Sciences 200303 US, vol. 983, Mar. 2003, pp. 170-180.

Widschwendter et al.: "Analysis Of Aberrant DNA Methylation And Human Papillomavirus DNA in Cervicovaginal Specimens To Detect Invasive Cervical Cancer And Its Precursors" Clinical Cancer Research, The American Association For Cancer Research, US, vol. 10, No. 10, May 15, 2004, pp. 3396-3400.

Yanagi et al., "Hepatitis C Virus: An Infectious Molecular Clone Of A Second Major Genotype (2A) And Lack Of Viability of Intertypic 1A And 2A Chimeras," Virology 262, pp. 250-263 (1999).

Zeschnigk et al., "A novel real-time PCR assay for quantitative analysis of methylated alleles (QAMA): analysis of the retinoblastoma locus," Nucleic Acid Research 2004, vol. 32, No. 16, pp. 1-5.

Christensen et al., "Intercalating nucleic acids containing insertions of 1-0-(1-pyrenylmethyl)glycerol: stabilisation of dsDNA and discrimination of DNA over RNA." Nucleic Acid Res. vol. 30, No. 22, pp. 4918-4925, (2002).

Clark et al., "High sensitivity mapping of methylated cytosines." Nucleic Acids Research, 22(15): 2990-2997 (1994).

Clark, et al., " Bisulphite genomic sequencing of methylated cytosines." Laboratory Methods for the Detection of Mutations and Polymorphisms in DNA. Graham R. Taylor, Ed. CRC Press, New York (1997), pp. 151-162.

NCBI Database Accession No. M24485, Dec. 5, 1994.

Dean et al., "Comprehensive human genome amplification using multiple displacement amplification." PNAS, 99(8): 5261-5266 (2002).

Eads et al., "MethylLight: a high-throughput assay to measure DNA methylation." Nucleic Acids Research, 28(8)e32: i-viii (2000).

Feil, et al., " Methylation analysis on individual chromoshomes: improved protocol for bisulphite genomic sequencing." (1994) Nucleic Acids Research 22(4): 695-696.

Frommer et al., " A genomic sequencing protocol that yields a positive display of 5-methylcytosine residues in individual DNA strands," Proc. Natl. Acad. Sci. 89: 1827-1831 (1992).

Grigoriev et al., "A Triple Helix-forming Oligonucleotide-Intercalator Conjugate Acts as a Transcriptional Repressor via Inhibition of NFkB Binding to Interleukin-2 Receptor α-Regulatory Sequence." Journal of Biological Chemistry, 267 (5): 3389-3395 (1992).

Grunau, et al., "Bisulfite genomic sequencing: systematic investigation of critical experimental parameters." Nucleic Acid Research, (2001) vol. 29, No. 13e65, pp. 1-7.

Hakelien et al., "Reprogramming fibroblasts to express T-cell functions using cell extracts." Nature Briotechnology, 20(5): 460-466 (2002).

Hakelien et al., "Novel approaches to transdifferentiation", Cloning and Stem Cells, 4: 379-387 (2002).

Herman, et al., "Methylation-specific PCR-: a novel PCR assay for methylation status of CpG islands." (1996) Proc. Natl. Acad. Sci. 93:9821-9826.

Hosono et al. "Unbiased Whole-Genome Amplification Directly from Clinical Samples." Genome Research; 13:954-964 (2003).

International Human Genome Sequencing Consrtium, "Initial sequencing and analysis of the human genome," Nature, 409(6822): 860-921 (2001).

International Preliminary Report on Patentability issued on the corresponding PCT Application No. PCT/AU2006/000698, dated Apr. 20, 2007.

International Search Report Issued on the corresponding PCT Application No. PCT/AU2006/000698, dated Aug. 1, 2006.

Kinoshita et al., "Methylation of the androgen receptor minimal promoter silences transcription in human prostate cancer." Cancer Research, 60(13): 3623-3630 (Jul. 1, 2000).

Kono, "Nuclear transfer and reprogramming." Reviews of Reproduction, vol. 2 No. 2, pp. 74-80 (May 1997).

Millar et al., "A distinct sequence (ATAAA) n separates methylated and unmethylated domains at the 5'-end of the GSTP1 CpG island," J. Biol. Chem., 275(32): 24893-24899 (2000).

Millar et al., "Detailed methylation analysis of the glutathione S-transferase pi (GSTP1) gene in prostate cancer," Oncogene 18(6): 1313-1324, (1999).

Monk, "Epigentic programming of differential gene expression in development and evolution" Dev. Genetics, vol. 17, pp. 188-197 (1995).

Newton et al., "The production of PCR products with 5' single-stranded tails using primers that incorporate novel phosphoramidite intermediates." Nucleic Acid Res. vol. 21 No. 5, pp. 1155-1162 (1993).

Nilsson et al., "Padlock Probes: Circularizing oligonucleotides for localized DNA Detection", Science; 265:2085-2088 (1994).

Office Action in U.S. Appl. No. 10/416,637 dated May 4, 2006.
Office Action in U.S. Appl. No. 10/428,310 dated Aug. 31, 2006.
Office Action in U.S. Appl. No. 10/428,310 dated Jan. 4, 2006.
Office Action in U.S. Appl. No. 10/428,310 dated Jul. 5, 2006.
Office Action in U.S. Appl. No. 10/428,310 dated Nov. 3, 2006.
Office Action in U.S. Appl. No. 10/536,633 dated Apr. 4, 2007.
Office Action in U.S. Appl. No. 10/536,633 dated Jan. 25, 2007.

Okada, et al., " Sequence Determination of Rat U5 RNA Unsing a Chemical Modification Procedure for Counteracting Sequence Compression." (1982) J. Biochem. 91: 1281-1291.

Olek, et al. " A modified and improved method for bisulphite based cytosine methylation analysis." (1996) Nucleic Acids Research, 24(24): 5064-5066.

Paulin et al., "Urea improves efficiency of bisulphite-mediated sequencing of 5'-methylcytosine in genomic DNA." Nucleic Acid Research, 26(21): 5009-5010 (Nov. 1, 1998).

Pietrobono et al., "Quantitative analysis of DNA demethylation and transcriptional reactivation of the FMR1 gene in fragile X cells treated with 5-azadeoxycytidine." Nucleic Acids Research, 30(14): 3278-3285 (2002).

Raizis et al., "A Bisulfite Method of 5-Methylcytosine mapping that minimizes template degradation", Anal. Biochem., 226: 161-166 (1995).

Rein et al., "Identifying 5-methylcytosine and related modifications in DNA genomes." Nucleic Acids Research, 26 (10): 2255-2264 (May 15, 1998).

Robertson et al., Blood 90: 4480-4484 (1997).

Robertson et al. "DNA methylation: past, present, and future directions." Carcinogenesis. 21(3): 461-467 (2000).

Sakaguchi et al. "Cautionary Note on the Use of dUMP-Containing PCR Primers with $Pfu$ and $Vent_R$® DNA Polymerases." Biotechniques; 21(3):368 & 370 (1996).

Sakashita et al., "Dynamic DNA Methylation change in the CpG island region of p15 during human myeloid development", J. Clin. Invest., 108: 1195-1204 (2001).

Shapiro et al., "Deamination of cytosine derivatives by bisulfite. Mechanism of the reaction," J. Am. Chem. Soc., 96: 906-912 (1974).

Specification and Preliminary Amendment from co-pending U.S. Appl. No. 10/555,465, filed Aug. 28, 2006.

Tada et al., "Embryonic germ cells induce epigenetic reprogramming of somatic nucleus in hybrid cells." The EMBO Journal, 16(21): 6510-6520 (1997).

Telenius et al. "Degenerate Oligonucleotide-Primed PCR: General Amplification of Target DNA by a Single Degenerate Primer." Genomics; 13(3):718-725 (1992).

Tohgi et al., " Decrease with age in methylcytosines in the promoter region of receptor for advanced glycated end products (RAGE) gene in autopsy human cortex", Molecular Brain Research, 65:124-128 (1999).

Venter et al., "The sequence of the human genome," Science, 292 (5523): 1304-1351(2001).

Warnecke et al., "Detection and measurement of PCR bias in quantitative methylation analysis of bisulphite-treated DNA," Nucleic Acids Research, vol. 25 No. 21, pp. 4422-4426, (1997).

Xiong et al., "COBRA: a sensititive and quantitative DNA methylation assay." (1997) Nucleic Acids Research, 25 (12): 2532-2534.

* cited by examiner

Figure 2

Blocker Specific Amplification

Genomic DNA sequence
CGGGTGACCCCTCCCCTGCCCTGTGAAGCGGGTGCCGGCGCGCCGAGGCCGCGAAGTTCGCTGCCTGCGGCGACTCCGGGCGCGGCGCACCTGCAGCATCTCCCG Bisulphite treated Methylated sequence
CGGGTGATTTTTTTTTTTCGTTTTCGTTGAAGCGGGTCGCGGCGCGTCGGAGGTCGCGAAGTTCGTTGTTTCGCGGCGATTTCGGGGAATGGGGTTAATTCGTAGTATTTTCG Bisulphite treated Unmethylated sequence
TGGGTGATTTTTTTTTTTGTTTTGTTTGTTTGTGAAGTTGGGTGTGTGTGTGATTTGGGGAATGGGGTTAATTTGTAGTATTTTTG

INA Blocker Specific PCR

5'-TTTTTTTTTTGTTTTGT-3'        3'-TACCCCAATTAAACATCATAAAAA-5'
PCR Primer#2                    PCR Primer#1

5'-GAAGCGGGTGTCGGCGC-3'         3'-GCGCCGC TAAAGCCCCT-5'
Methyl Blocker#2                Methyl Blocker#1

5'-GAAGTGGGTGTTGGTGT-3'         3'-ACACCTACTAAAACCCCT-5'
Unmethyl Blocker#2              Unmethyl Blocker#1

Figure 3

A. Unconverted sequence

```
CGGGTGACCCCTCTCCCCTGCCCTGTGAAGCGCCTGCCGCCGCCCCCGA
  |||||                          |||||||||
  CCACTAAAAAA                    AAACAGCAGCAAAA
  PCR Primer#1                   Methyl blocker#1
```

B. Bisulphite treated Methylated sequence

```
CGGGTGATTTTTTTTTTTGTTTTGTGAAGCGCCTGTCGTCGTTTTCGA
  |||||||||||                  ||||||||||||
  CCACTAAAAAA                  AAACAGCAGCAAAA
  PCR Primer#1                 Methyl blocker#1
```

C. Bisulphite treated Unmethylated sequence

```
TGGGTGATTTTTTTTTTTGTTTTGTGAAGTGTTTGTTGTTGTTTTTGA
  |||||||||||                 |||||| || ||||||
  CCACTAAAAAA                 AAACAGCAGCAAAA
  PCR Primer#1                Methyl blocker#1
```

D. Regional non-converted sequence

```
CGGGTGATTTTTTTCCCCTGCCCTGTGAAGCGCCTGCCGTCGCCCCCGA
  |||||||||||                  ||  ||||||
  CCACTAAAAAA                  AAACAGCAGCAAAA
  PCR Primer#1                 Methyl blocker#1
```

Figure 4

A. Unconverted sequence

```
CGGGTGACCCCTCTCCCCTGCCCTGTGAAGCGCCTGCCGCCGCCCCGA
  |||||    |                    ||||| ||  ||    ||
  CCACTAAAAAA                    AAACAACAACAAAA
  PCR Primer#1                   Unmethyl blocker#1
```

B. Bisulphite treated Methylated sequence

```
CGGGTGATTTTTTTTTTTGTTTTGTGAAGCGCCTGTCGTCGTTTTCGA
  ||||||||||||                 ||||| || ||  ||||
  CCACTAAAAAA                   AAACAACAACAAAA
  PCR Primer#1                  Unmethyl blocker#1
```

C. Bisulphite treated Unmethylated sequence

```
TGGGTGATTTTTTTTTTTGTTTTGTGAAGTGTTTGTTGTTGTTTTTGA
 ||||||||||||                ||||||||||||||||
 CCACTAAAAAA                  AAACAACAACAAAA
 PCR Primer#1                 Unmethyl blocker#1
```

D. Regional non-converted sequence

```
CGGGTGATTTTTTTTCCCCTGCCCTGTGAAGCGCCTGCCGCCGCCCCGA
  ||||||||||||                   ||  ||  ||    ||
  CCACTAAAAAA                    AAACAACAACAAAA
  PCR Primer#1                   Unmethyl blocker#1
```

Figure 5

A. Unconverted sequence

<u>CG</u>GGTGACCCCTCTCCCCTGCCCTGTGAAG<u>CG</u>CCTGC<u>CG</u>C<u>CG</u>CCCC<u>CG</u>A
　|||||　　　　|　　　　　　　　|||||||||||||||
　CCACTAAAAAA　　　　　　　　　　GGACG<u>GC</u>G<u>GC</u>GGGG

PCR Primer#1　　　　　　　　　　non converted blocker#1

B. Bisulphite treated Methylated sequence

<u>CG</u>GGTGATTTTTTTTTTTGTTTTGTGAAG<u>CG</u>CCTGT<u>CG</u>T<u>CG</u>TTTT<u>CG</u>A
　||||||||||||　　　　　　　　　||　||　||
　CCACTAAAAAA　　　　　　　　　　GGACG<u>GC</u>G<u>GC</u>GGGG

PCR Primer#1　　　　　　　　　　non converted blocker#1

C. Bisulphite treated Unmethylated sequence

<u>TG</u>GGTGATTTTTTTTTTTGTTTTGTGAAG<u>TG</u>TTTGT<u>TG</u>T<u>TG</u>TTTT<u>TG</u>A
　||||||||||||　　　　　　　　　||　||　||
　CCACTAAAAAA　　　　　　　　　　GGACG<u>GC</u>G<u>GC</u>GGGG

PCR Primer#1　　　　　　　　　　non converted blocker#1

D. Regional non-converted sequence

<u>CG</u>GGTGATTTTTTTTCCCCTGCCCTGTGAAG<u>CG</u>CCTGC<u>CG</u>C<u>CG</u>CCCC<u>CG</u>A
　|||||||||||||　　　　　　　　　|||||||||||||||
　CCACTAAAAAA　　　　　　　　　　　GGACG<u>GC</u>G<u>GC</u>GGGG

PCR Primer#1　　　　　　　　　　non converted blocker#1

1. Conventional PCR
2. MSP methylated detection
3. MSP unmethylated detection
4. INA blocker methylation block
5. INA blocker unmethylation block
M=DNA marker ladder

Figure 7
INA blockers applied to genomic DNA samples
7A. Results of PCR amplification with the addition of unmethylated blockers
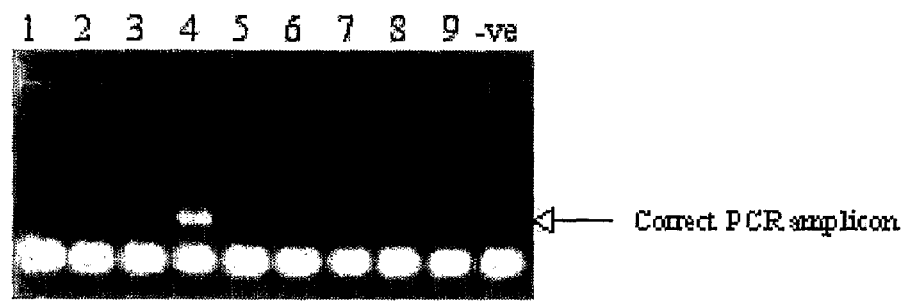
7B Results of PCR amplification with the addition of methylated blockers
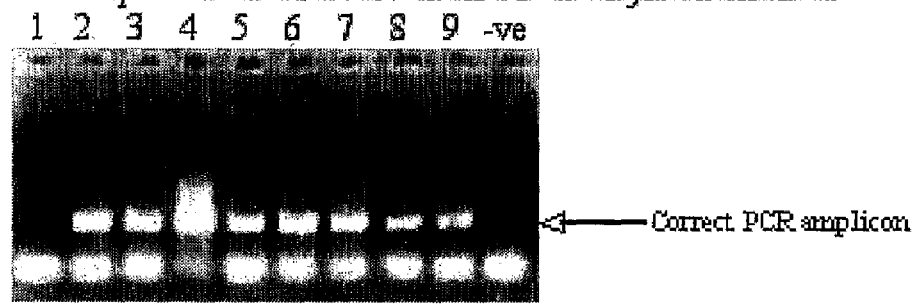
7C Control reaction no blockers added
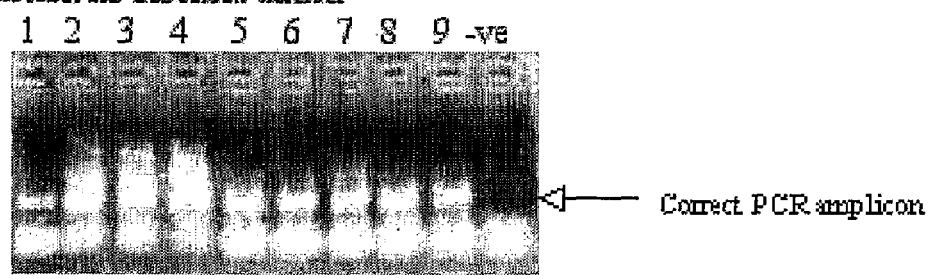

SEQUENCE LISTING

<160> NUMBER OF SEQ ID NOS: 97

<210> SEQ ID NO 1
<211> LENGTH: 34
<212> TYPE: DNA
<213> ORGANISM: artificial sequence
<220> FEATURE:
<223> OTHER INFORMATION: Oligonucleotide primer

<400> SEQUENCE: 1
tyttcggtta gyttgcgcgg cgaytttcgg ygga                                    34

<210> SEQ ID NO 2
<211> LENGTH: 34
<212> TYPE: DNA
<213> ORGANISM: Artificial sequence
<220> FEATURE:
<223> OTHER INFORMATION: Oligonucleotide primer

<400> SEQUENCE: 2

-continued tytttggtta gyttgtgtgg tgayttttgg ygga                                    34

<210> SEQ ID NO 3
<211> LENGTH: 34
<212> TYPE: DNA
<213> ORGANISM: Artificial sequence
<220> FEATURE:
<223> OTHER INFORMATION: Oligonucleotide primer

<400> SEQUENCE: 3
cycccggcca gyctgcgcgg cgayctccgg ygga                                    34

<210> SEQ ID NO 4
<211> LENGTH: 34
<212> TYPE: DNA
<213> ORGANISM: Artificial sequence
<220> FEATURE:
<223> OTHER INFORMATION: Oligonucleotide primer

<400> SEQUENCE: 4
ttaytaacga aayactyacg acgacgaaac ytcc                                    34

<210> SEQ ID NO 5
<211> LENGTH: 34
<212> TYPE: DNA
<213> ORGANISM: Artificial sequence
<220> FEATURE:
<223> OTHER INFORMATION: Oligonucleotide primer

<400> SEQUENCE: 5
ttaytaacaa aayactyaca acaacaaaac ytcc                                    34

<210> SEQ ID NO 6
<211> LENGTH: 34
<212> TYPE: DNA
<213> ORGANISM: Artificial sequence
<220> FEATURE:
<223> OTHER INFORMATION: Oligonucleotide primer

<400> SEQUENCE: 6
tggytggcga agyactygcg gcggcgaaac ytcc                                    34

<210> SEQ ID NO 7
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 7
ttyagggcgt yttttytgc ggtcgacgty t                                        31

<210> SEQ ID NO 8
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 8
ttyagggtgt yttttytgt ggttgatgty t                                        31

<210> SEQ ID NO 9
<211> LENGTH: 31
<212> TYPE: DNA
<213> ORGANISM: Artificial sequence

```
<220> FEATURE:
<223> OTHER INFORMATION: Oligonucleotide primer

<400> SEQUENCE: 9
ccyagggcgc yccctcytgc ggccgacgcy c                                    31

<210> SEQ ID NO 10
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 10
atyaatcccg ccyccgctyc cgccccayat a                                    31

<210> SEQ ID NO 11
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 11
atyaatccca ccyccactyc caccccayat a                                    31

<210> SEQ ID NO 12
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 12
gtyggtcccg ccyccgctyc cgccccaygt g                                    31

<210> SEQ ID NO 13
<211> LENGTH: 27
<212> TYPE: DNA
<213> ORGANISM: human

<400> SEQUENCE: 13
tttgttgttt gtttattttt taggttt                                         27

<210> SEQ ID NO 14
<211> LENGTH: 26
<212> TYPE: DNA
<213> ORGANISM: human

<400> SEQUENCE: 14
aacctaatac tactaattaa ccccat                                          26

<210> SEQ ID NO 15
<211> LENGTH: 26
<212> TYPE: DNA
<213> ORGANISM: human

<400> SEQUENCE: 15
ggatttggga aagagggaaa ggtttt                                          26

<210> SEQ ID NO 16
<211> LENGTH: 24
<212> TYPE: DNA
<213> ORGANISM: human
```

<400> SEQUENCE: 16
actaaaaact ctaaacccca tccc                                           24

<210> SEQ ID NO 17
<211> LENGTH: 111
<212> TYPE: DNA
<213> ORGANISM: Artificial sequence
<220> FEATURE:
<223> OTHER INFORMATION: Oligonucleotide primer

<400> SEQUENCE: 17
cgggtgaccc ctctcccctg ccctgtgaag cgggtgccgg cgcgccgagg ccgcgaagtt    60
cgctgcctgc gcggcgactc cggggaatgg ggccacctgc agcatctccc g            111

<210> SEQ ID NO 18
<211> LENGTH: 112
<212> TYPE: DNA
<213> ORGANISM: Artificial sequence
<220> FEATURE:
<223> OTHER INFORMATION: Oligonucleotide primer

<400> SEQUENCE: 18
cgggtgattt tttttttttg ttttgtgaag cgggtgtcgg cgcgtcgagg tcgcgaagtt    60
cgttgtttgc gcggcgattt cggggaatgg ggttaatttg tagtattttt cg           112

<210> SEQ ID NO 19
<211> LENGTH: 112
<212> TYPE: DNA
<213> ORGANISM: Artificial sequence
<220> FEATURE:
<223> OTHER INFORMATION: Oligonucleotide primer

<400> SEQUENCE: 19
tgggtgattt tttttttttg ttttgtgaag tgggtgttgg tgtgttgagg ttgtgaagtt    60
tgttgtttgt gtggtgattt tggggaatgg ggttaatttg tagtattttt tg           112

<210> SEQ ID NO 20
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 20
tttttttttt tttgttttgt                                                20

<210> SEQ ID NO 21
<211> LENGTH: 24
<212> TYPE: DNA
<213> ORGANISM: Artificial sequence
<220> FEATURE:
<223> OTHER INFORMATION: Oligonucleotide primer

<400> SEQUENCE: 21
taccccaatt aaacatcata aaaa                                           24

<210> SEQ ID NO 22
<211> LENGTH: 17
<212> TYPE: DNA
<213> ORGANISM: Artificial sequence
<220> FEATURE:
<223> OTHER INFORMATION: Oligonucleotide primer

<400> SEQUENCE: 22
gaagcgggtg tcggcgc                                              17

<210> SEQ ID NO 23
<211> LENGTH: 17
<212> TYPE: DNA
<213> ORGANISM: Artificial sequence
<220> FEATURE:
<223> OTHER INFORMATION: Oligonucleotide primer

<400> SEQUENCE: 23
gcgccgctaa agcccct                                              17

<210> SEQ ID NO 24
<211> LENGTH: 17
<212> TYPE: DNA
<213> ORGANISM: Artificial sequence
<220> FEATURE:
<223> OTHER INFORMATION: Oligonucleotide primer

<400> SEQUENCE: 24
gaagtgggtg ttggtgt                                              17

<210> SEQ ID NO 25
<211> LENGTH: 18
<212> TYPE: DNA
<213> ORGANISM: Artificial sequence
<220> FEATURE:
<223> OTHER INFORMATION: Oligonucleotide primer

<400> SEQUENCE: 25
acacctacta aaacccct                                             18

<210> SEQ ID NO 26
<211> LENGTH: 49
<212> TYPE: DNA
<213> ORGANISM: Artificial sequence
<220> FEATURE:
<223> OTHER INFORMATION: Oligonucleotide primer

<400> SEQUENCE: 26
cgggtgaccc ctctccccctg ccctgtgaag cgcctgccgc cgccccga          49

<210> SEQ ID NO 27
<211> LENGTH: 49
<212> TYPE: DNA
<213> ORGANISM: Artificial sequence
<220> FEATURE:
<223> OTHER INFORMATION: Oligonucleotide primer

<400> SEQUENCE: 27
cgggtgattt tttttttttg ttttgtgaag cgcctgtcgt cgttttcga          49

<210> SEQ ID NO 28
<211> LENGTH: 49
<212> TYPE: DNA
<213> ORGANISM: Artificial sequence
<220> FEATURE:
<223> OTHER INFORMATION: Oligonucleotide primer

<400> SEQUENCE: 28
tgggtgattt tttttttttg ttttgtgaag tgtttgttgt tgttttga          49

<210> SEQ ID NO 29
<211> LENGTH: 50
<212> TYPE: DNA

```
<213> ORGANISM: Artificial sequence
<220> FEATURE:
<223> OTHER INFORMATION: Oligonucleotide primer

<400> SEQUENCE: 29
cgggtgattt ttttccccct gccctgtgaa gcgcctgccg tcgccccga          50

<210> SEQ ID NO 30
<211> LENGTH: 11
<212> TYPE: DNA
<213> ORGANISM: Artificial sequence
<220> FEATURE:
<223> OTHER INFORMATION: Oligonucleotide primer

<400> SEQUENCE: 30
ccactaaaaa a                                                   11

<210> SEQ ID NO 31
<211> LENGTH: 14
<212> TYPE: DNA
<213> ORGANISM: Artificial sequence
<220> FEATURE:
<223> OTHER INFORMATION: Oligonucleotide primer

<400> SEQUENCE: 31
aaacagcagc aaaa                                                14

<210> SEQ ID NO 32
<211> LENGTH: 14
<212> TYPE: DNA
<213> ORGANISM: Artificial sequence
<220> FEATURE:
<223> OTHER INFORMATION: Oligonucleotide primer

<400> SEQUENCE: 32
aaacaacaac aaaa                                                14

<210> SEQ ID NO 33
<211> LENGTH: 14
<212> TYPE: DNA
<213> ORGANISM: Artificial sequence
<220> FEATURE:
<223> OTHER INFORMATION: Oligonucleotide primer

<400> SEQUENCE: 33
ggacggcggc gggg                                                14

<210> SEQ ID NO 34
<211> LENGTH: 29
<212> TYPE: DNA
<213> ORGANISM: Artificial sequence
<220> FEATURE:
<223> OTHER INFORMATION: Oligonucleotide primer

<400> SEQUENCE: 34
gattyttgcg yacgcgyttc gtatyttg                                 29

<210> SEQ ID NO 35
<211> LENGTH: 27
<212> TYPE: DNA
<213> ORGANISM: Artificial sequence
<220> FEATURE:
<223> OTHER INFORMATION: Oligonucleotide primer

<400> SEQUENCE: 35
tttttggttt agttgaaaaa ggaattt                                  27
```

<210> SEQ ID NO 36
<211> LENGTH: 30
<212> TYPE: DNA
<213> ORGANISM: Artificial sequence
<220> FEATURE:
<223> OTHER INFORMATION: Oligonucleotide primer

<400> SEQUENCE: 36
gttyaacgay tcggtcgtyt cggttyattg                                   30

<210> SEQ ID NO 37
<211> LENGTH: 30
<212> TYPE: DNA
<213> ORGANISM: Artificial sequence
<220> FEATURE:
<223> OTHER INFORMATION: Oligonucleotide primer

<400> SEQUENCE: 37
ttaggagttt tttttttagaa gtaatttagg                                  30

<210> SEQ ID NO 38
<211> LENGTH: 28
<212> TYPE: DNA
<213> ORGANISM: Artificial sequence
<220> FEATURE:
<223> OTHER INFORMATION: Oligonucleotide primer

<400> SEQUENCE: 38
ccycgcgccg cgyacgctya accyaaac                                     28

<210> SEQ ID NO 39
<211> LENGTH: 32
<212> TYPE: DNA
<213> ORGANISM: Artificial sequence
<220> FEATURE:
<223> OTHER INFORMATION: Oligonucleotide primer

<400> SEQUENCE: 39
acttccaaaa actatgtgac cttctccact aa                                32

<210> SEQ ID NO 40
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 40
aactccgtty aaaaytccgc gccgyactty c                                 31

<210> SEQ ID NO 41
<211> LENGTH: 25
<212> TYPE: DNA
<213> ORGANISM: Artificial sequence
<220> FEATURE:
<223> OTHER INFORMATION: Oligonucleotide primer

<400> SEQUENCE: 41
aaaccctaaa accccaacta cctaa                                        25

<210> SEQ ID NO 42
<211> LENGTH: 29
<212> TYPE: DNA
<213> ORGANISM: Artificial sequence
<220> FEATURE:

```
<223> OTHER INFORMATION: Oligonucleotide primer

<400> SEQUENCE: 42
gattyttgtg yatgtgyttt gtatytttg                                29

<210> SEQ ID NO 43
<211> LENGTH: 30
<212> TYPE: DNA
<213> ORGANISM: Artificial sequence
<220> FEATURE:
<223> OTHER INFORMATION: Oligonucleotide primer

<400> SEQUENCE: 43
gttyaatgay ttggttgtyt tggttyattg                               30

<210> SEQ ID NO 44
<211> LENGTH: 28
<212> TYPE: DNA
<213> ORGANISM: Artificial sequence
<220> FEATURE:
<223> OTHER INFORMATION: Oligonucleotide primer

<400> SEQUENCE: 44
ccycacacca cayacactya accyaaac                                 28

<210> SEQ ID NO 45
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 45
aactccatty aaaaytccac accayactty c                             31

<210> SEQ ID NO 46
<211> LENGTH: 29
<212> TYPE: DNA
<213> ORGANISM: Artificial sequence
<220> FEATURE:
<223> OTHER INFORMATION: Oligonucleotide primer

<400> SEQUENCE: 46
gactyccgcg yacgcgytcc gcacycctg                                29

<210> SEQ ID NO 47
<211> LENGTH: 30
<212> TYPE: DNA
<213> ORGANISM: Artificial sequence
<220> FEATURE:
<223> OTHER INFORMATION: Oligonucleotide primer

<400> SEQUENCE: 47
gctyaacgay ccggccgcyt cggccyactg                               30

<210> SEQ ID NO 48
<211> LENGTH: 28
<212> TYPE: DNA
<213> ORGANISM: Artificial sequence
<220> FEATURE:
<223> OTHER INFORMATION: Oligonucleotide primer

<400> SEQUENCE: 48
ccycgcgccg cgygcgctyg gccyagac                                 28
```

<210> SEQ ID NO 49
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 49
gactccgtty gggaytccgc gccgygctty c                              31

<210> SEQ ID NO 50
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 50
ggtttyacga yagcgttttty ttcgtagygc g                             31

<210> SEQ ID NO 51
<211> LENGTH: 29
<212> TYPE: DNA
<213> ORGANISM: Artificial sequence
<220> FEATURE:
<223> OTHER INFORMATION: Oligonucleotide primer

<400> SEQUENCE: 51
attgaaatgt tttttagaga agtaattttt                                29

<210> SEQ ID NO 52
<211> LENGTH: 32
<212> TYPE: DNA
<213> ORGANISM: Artificial sequence
<220> FEATURE:
<223> OTHER INFORMATION: Oligonucleotide primer

<400> SEQUENCE: 52
gaygcggcgg gtytttcgty tttcgttttty ag                            32

<210> SEQ ID NO 53
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 53
gtgggtttaa gggatttgat tt                                        22

<210> SEQ ID NO 54
<211> LENGTH: 32
<212> TYPE: DNA
<213> ORGANISM: Artificial sequence
<220> FEATURE:
<223> OTHER INFORMATION: Oligonucleotide primer

<400> SEQUENCE: 54
ycccgaaact ccayaatcga tcyccgaaty tc                             32

<210> SEQ ID NO 55
<211> LENGTH: 24
<212> TYPE: DNA
<213> ORGANISM: Artificial sequence
<220> FEATURE:
<223> OTHER INFORMATION: Oligonucleotide primer

```
<210> SEQ ID NO 56
<211> LENGTH: 28
<212> TYPE: DNA
<213> ORGANISM: Artificial sequence
<220> FEATURE:
<223> OTHER INFORMATION: Oligonucleotide primer

<400> SEQUENCE: 56
yctaaaayaa cccgaayatc ccgaacyc                                    28

<210> SEQ ID NO 57
<211> LENGTH: 25
<212> TYPE: DNA
<213> ORGANISM: Artificial sequence
<220> FEATURE:
<223> OTHER INFORMATION: Oligonucleotide primer

<400> SEQUENCE: 57
aactaacaaa aaactaccta taacc                                       25

<210> SEQ ID NO 58
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 58
ggtttyatga yagtgttttty tttgtagygt g                               31

<210> SEQ ID NO 59
<211> LENGTH: 32
<212> TYPE: DNA
<213> ORGANISM: Artificial sequence
<220> FEATURE:
<223> OTHER INFORMATION: Oligonucleotide primer

<400> SEQUENCE: 59
gaygtggtgg gtytttttgty ttttgttttyt ag                             32

<210> SEQ ID NO 60
<211> LENGTH: 32
<212> TYPE: DNA
<213> ORGANISM: Artificial sequence
<220> FEATURE:
<223> OTHER INFORMATION: Oligonucleotide primer

<400> SEQUENCE: 60
ycccaaaact cycaaatcaa tcyccaaaty tc                               32

<210> SEQ ID NO 61
<211> LENGTH: 28
<212> TYPE: DNA
<213> ORGANISM: Artificial sequence
<220> FEATURE:
<223> OTHER INFORMATION: Oligonucleotide primer

<400> SEQUENCE: 61
yctaaaayaa cccaaayatc ccaaacyc                                    28

<210> SEQ ID NO 62
<211> LENGTH: 31
```

(SEQ ID NO: 55 continued)

accccttta tacataatta aaac                                         24

<210> SEQ ID NO 62
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 62
ggttcyacga yagcgcctcy ctcgcagygc g           31

<210> SEQ ID NO 63
<211> LENGTH: 32
<212> TYPE: DNA
<213> ORGANISM: Artificial sequence
<220> FEATURE:
<223> OTHER INFORMATION: Oligonucleotide primer

<400> SEQUENCE: 63
gaygcggcgg gcytctcgcy tcccgctccy ag          32

<210> SEQ ID NO 64
<211> LENGTH: 32
<212> TYPE: DNA
<213> ORGANISM: Artificial sequence
<220> FEATURE:
<223> OTHER INFORMATION: Oligonucleotide primer

<400> SEQUENCE: 64
ycccggagct ccaygatcga tcyccgagty tc          32

<210> SEQ ID NO 65
<211> LENGTH: 28
<212> TYPE: DNA
<213> ORGANISM: Artificial sequence
<220> FEATURE:
<223> OTHER INFORMATION: Oligonucleotide primer

<400> SEQUENCE: 65
yctggaayag cccggaygtc ccgggycc               28

<210> SEQ ID NO 66
<211> LENGTH: 30
<212> TYPE: DNA
<213> ORGANISM: Artificial sequence
<220> FEATURE:
<223> OTHER INFORMATION: Oligonucleotide primer

<400> SEQUENCE: 66
gttygggttc gtcgytcgtt cgtygtttyg             30

<210> SEQ ID NO 67
<211> LENGTH: 27
<212> TYPE: DNA
<213> ORGANISM: Artificial sequence
<220> FEATURE:
<223> OTHER INFORMATION: Oligonucleotide primer

<400> SEQUENCE: 67
ttgtaaaatg ggttggtagt tgtattt                27

<210> SEQ ID NO 68
<211> LENGTH: 27
<212> TYPE: DNA
<213> ORGANISM: Artificial sequence
<220> FEATURE:
<223> OTHER INFORMATION: Oligonucleotide primer

<400> SEQUENCE: 68

```
gttyagcgty tcgtcgtaty gttaygg                                27
```

<210> SEQ ID NO 69
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 69

```
ttgaaaagga tgtgttgatg tt                                     22
```

<210> SEQ ID NO 70
<211> LENGTH: 28
<212> TYPE: DNA
<213> ORGANISM: Artificial sequence
<220> FEATURE:
<223> OTHER INFORMATION: Oligonucleotide primer

<400> SEQUENCE: 70

```
aytcgacccg yacaaayacg cgacayac                               28
```

<210> SEQ ID NO 71
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 71

```
aatcttaaaa acatctaaat tc                                     22
```

<210> SEQ ID NO 72
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 72

```
ycccgcccat cyccgcccaa yaccgaaaya c                           31
```

<210> SEQ ID NO 73
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 73

```
acaaaaaacc caatctacaa c                                      21
```

<210> SEQ ID NO 74
<211> LENGTH: 30
<212> TYPE: DNA
<213> ORGANISM: Artificial sequence
<220> FEATURE:
<223> OTHER INFORMATION: Oligonucleotide primer

<400> SEQUENCE: 74

```
gttygggttt gttgyttgtt tgtygtttyg                             30
```

<210> SEQ ID NO 75
<211> LENGTH: 27
<212> TYPE: DNA
<213> ORGANISM: Artificial sequence -continued
<220> FEATURE:
<223> OTHER INFORMATION: Oligonucleotide primer

<400> SEQUENCE: 75
gttyagtgty ttgttgtaty gttaygg                                    27

<210> SEQ ID NO 76
<211> LENGTH: 28
<212> TYPE: DNA
<213> ORGANISM: Artificial sequence
<220> FEATURE:
<223> OTHER INFORMATION: Oligonucleotide primer

<400> SEQUENCE: 76
aytcaaccca yacaaayaca caacayac                                   28

<210> SEQ ID NO 77
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 77
ycccacccat cyccacccaa yaccaaaaya c                               31

<210> SEQ ID NO 78
<211> LENGTH: 30
<212> TYPE: DNA
<213> ORGANISM: Artificial sequence
<220> FEATURE:
<223> OTHER INFORMATION: Oligonucleotide primer

<400> SEQUENCE: 78
gctygggctc gccgyccgct cgtygcctyg                                 30

<210> SEQ ID NO 79
<211> LENGTH: 27
<212> TYPE: DNA
<213> ORGANISM: Artificial sequence
<220> FEATURE:
<223> OTHER INFORMATION: Oligonucleotide primer

<400> SEQUENCE: 79
gctyagcgcy ccgccgtaty gtcaygg                                    27

<210> SEQ ID NO 80
<211> LENGTH: 28
<212> TYPE: DNA
<213> ORGANISM: Artificial sequence
<220> FEATURE:
<223> OTHER INFORMATION: Oligonucleotide primer

<400> SEQUENCE: 80
aytcgacccg yacaggygcg cggcaygc                                   28

<210> SEQ ID NO 81
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 81
ycccgcccat cyccgcccaa ygccggggya c                               31

```
<210> SEQ ID NO 82
<211> LENGTH: 30
<212> TYPE: DNA
<213> ORGANISM: Artificial sequence
<220> FEATURE:
<223> OTHER INFORMATION: Oligonucleotide primer

<400> SEQUENCE: 82
gyttttyggg gcgtgtyagg tcgttttygg                                        30

<210> SEQ ID NO 83
<211> LENGTH: 24
<212> TYPE: DNA
<213> ORGANISM: Artificial sequence
<220> FEATURE:
<223> OTHER INFORMATION: Oligonucleotide primer

<400> SEQUENCE: 83
ggtaattgtt tttaaaaggg ttat                                              24

<210> SEQ ID NO 84
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 84
gygttaggcg gttyagggcg tcgtyacggy t                                      31

<210> SEQ ID NO 85
<211> LENGTH: 24
<212> TYPE: DNA
<213> ORGANISM: Artificial sequence
<220> FEATURE:
<223> OTHER INFORMATION: Oligonucleotide primer

<400> SEQUENCE: 85
gtttttattt tagagggtag ttgg                                              24

<210> SEQ ID NO 86
<211> LENGTH: 28
<212> TYPE: DNA
<213> ORGANISM: Artificial sequence
<220> FEATURE:
<223> OTHER INFORMATION: Oligonucleotide primer

<400> SEQUENCE: 86
tayaccgaya cgcctccyat cgtatcyc                                          28

<210> SEQ ID NO 87
<211> LENGTH: 29
<212> TYPE: DNA
<213> ORGANISM: Artificial sequence
<220> FEATURE:
<223> OTHER INFORMATION: Oligonucleotide primer

<400> SEQUENCE: 87
attaaactaa ttatcataca ccaccaaaa                                         29

<210> SEQ ID NO 88
<211> LENGTH: 29
<212> TYPE: DNA
<213> ORGANISM: Artificial sequence
<220> FEATURE:
<223> OTHER INFORMATION: Oligonucleotide primer
```

```
<400> SEQUENCE: 88
cttyatacgc gcgayaaaaa yaacgtytc                                          29

<210> SEQ ID NO 89
<211> LENGTH: 30
<212> TYPE: DNA
<213> ORGANISM: Artificial sequence
<220> FEATURE:
<223> OTHER INFORMATION: Oligonucleotide primer

<400> SEQUENCE: 89
atataaataa aatccaacac caaactaaac                                         30

<210> SEQ ID NO 90
<211> LENGTH: 30
<212> TYPE: DNA
<213> ORGANISM: Artificial sequence
<220> FEATURE:
<223> OTHER INFORMATION: Oligonucleotide primer

<400> SEQUENCE: 90
gyttttyggg gtgtgtyagg ttgttttygg                                         30

<210> SEQ ID NO 91
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 91
gygttaggtg gttyagggtg ttgtyatggy t                                       31

<210> SEQ ID NO 92
<211> LENGTH: 28
<212> TYPE: DNA
<213> ORGANISM: Artificial sequence
<220> FEATURE:
<223> OTHER INFORMATION: Oligonucleotide primer

<400> SEQUENCE: 92
tayaccaaya cacctccyat catatcyc                                           28

<210> SEQ ID NO 93
<211> LENGTH: 29
<212> TYPE: DNA
<213> ORGANISM: Artificial sequence
<220> FEATURE:
<223> OTHER INFORMATION: Oligonucleotide primer

<400> SEQUENCE: 93
cttyatacac acaayaaaaa yaacatytc                                          29

<210> SEQ ID NO 94
<211> LENGTH: 30
<212> TYPE: DNA
<213> ORGANISM: Artificial sequence
<220> FEATURE:
<223> OTHER INFORMATION: Oligonucleotide primer

<400> SEQUENCE: 94
gycccthggg gcgtgcyagg ccgccctygg                                         30

<210> SEQ ID NO 95
```

-continued

```
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 95
gygccaggcg gccyagggcg ccgcyacggy c                                  31

<210> SEQ ID NO 96
<211> LENGTH: 28
<212> TYPE: DNA
<213> ORGANISM: Artificial sequence
<220> FEATURE:
<223> OTHER INFORMATION: Oligonucleotide primer

<400> SEQUENCE: 96
tgygccggyg cgcctccyat cgtgtycc                                      28

<210> SEQ ID NO 97
<211> LENGTH: 29
<212> TYPE: DNA
<213> ORGANISM: Artificial sequence
<220> FEATURE:
<223> OTHER INFORMATION: Oligonucleotide primer

<400> SEQUENCE: 97
cttygtgcgc gcggyaagag yggcgtytc                                     29
```

US 7,803,580 B2

AMPLIFICATION BLOCKER COMPRISING INTERCALATING NUCLEIC ACIDS (INA) CONTAINING INTERCALATING PSEUDONUCLEOTIDES (IPN)

RELATED APPLICATIONS

This application is the U.S. National Phase filing under 35 U.S.C. §371 of PCT/AU2005/001374, filed Sep. 9, 2005, which designated the United States and was published in English on Mar. 16, 2006, which claims priority under 35 U.S.C. §119(a)-(d) to Australian Patent Application No. 2004905213, filed Sep. 10, 2004. The content of these applications is incorporated herein by reference in their entireties.

TECHNICAL FIELD

The invention relates to nucleic acid detection assays and in particular to improved assays using blockers of DNA amplification. The invention also relates to novel blockers of DNA amplification and methods suitable for the specific and sensitive detection of 5-methyl cytosine bases in nucleic acids.

BACKGROUND ART

A number of procedures are presently available for the detection of specific nucleic acid molecules. These procedures typically depend on sequence-dependent hybridisation between the target nucleic acid and nucleic acid probes which may range in length from short oligonucleotides (20 bases or less) to sequences of many kilobases (kb).

The most widely used method for amplification of specific sequences from within a population of nucleic acid sequences is that of polymerase chain reaction (PCR) (Dieffenbach C and Dveksler G eds. PCR Primer: A Laboratory Manual. Cold Spring Harbor Press, Plainview N.Y.). In this amplification method, oligonucleotides, generally 15 to 30 nucleotides in length of complementary strands and at either end of the region to be amplified, are used to prime DNA synthesis on denatured single-stranded DNA. Successive cycles of denaturation, primer hybridisation and DNA strand synthesis using thermostable DNA polymerases allows exponential amplification of the sequences between the primers. RNA sequences can be amplified by first copying the RNA to DNA using reverse transcriptase to produce a cDNA copy. Amplified DNA fragments can be detected by a variety of means including gel electrophoresis, blotting, hybridisation with labelled probes, use of tagged primers that allow subsequent identification (eg. by an enzyme linked assay), use of fluorescently-tagged primers that give rise to a signal upon hybridisation with the target DNA (eg. Beacon and TaqMan systems).

As well as PCR, a variety of other techniques have been developed for detection and amplification of specific nucleotide sequences. One example is the ligase chain reaction (Barany F Genetic disease detection and DNA amplification using cloned thermostable ligase. Proc. Natl. Acad. Sci. USA 88:189-193 (1991)).

For direct detection, the target nucleic acid is most commonly separated on the basis of size by gel electrophoresis and transferred to a solid support prior to hybridisation with a probe complementary to the target sequence (Southern and Northern blotting). The probe may be a natural nucleic acid or analogue such as peptide nucleic acid (PNA) or locked nucleic acid (LNA). The probe may be directly labelled (eg with $^{32}P$) or an indirect detection procedure may be used. Indirect procedures usually rely on incorporation into the probe of a "tag" such as biotin or digoxigenin and the probe is then detected by means such as enzyme-linked substrate conversion or chemiluminescence.

Another method for direct detection of nucleic acid that has been used widely is "sandwich" hybridisation. In this method, a capture probe is coupled to a solid support and the target nucleic acid, in solution, is hybridised with the bound probe. Unbound target nucleic acid is washed away and the bound nucleic acid is detected using a second probe that hybridises to the target sequences. Detection may use direct or indirect methods as outlined above. The "branched DNA" signal detection system is an example that uses the sandwich hybridization principle (Urdea M S et al. Branched DNA amplification multimers for the sensitive, direct detection of human hepatitis viruses. Nucleic Acids Symp Ser. 1991; (24): 197-200).

A rapidly growing area that uses nucleic acid hybridisation for direct detection of nucleic acid sequences is that of DNA micro-arrays (Young R A Biomedical discovery with DNA arrays. Cell 102: 9-15 (2000); Watson A New tools. A new breed of high tech detectives. Science 289:850-854 (2000)). In this process, individual nucleic acid species, that may range from oligonucleotides to longer sequences such as cDNA clones, are fixed to a solid support in a grid pattern. A tagged or labelled nucleic acid population is then hybridised with the array and the level of hybridisation with each spot in the array quantified. Most commonly, radioactively- or fluorescently-labelled nucleic acids (eg. cDNAs) were used for hybridisation, though other detection systems can be employed.

Currently, the method of choice to detect methylation changes in DNA, such as were found in the GSTP1 gene promoter in prostate cancer, are dependent on PCR amplification of such sequences after bisulphite modification of DNA. In bisulphite-treated DNA, cytosines are converted to uracils (and hence amplified as thymines during PCR) while methylated cytosines are non-reactive and remain as cytosines (Frommer M, McDonald L E, Millar D S, Collis C M, Watt F, Grigg G W, Molloy P L and Paul C L. A genomic sequencing protocol which yields a positive display of 5-methyl cytosine residues in individual DNA strands. PNAS 89: 1827-1831 (1992); Clark S J, Harrison J, Paul C L and Frommer M. High sensitivity mapping of methylated cytosines. Nucleic Acids Res. 22: 2990-2997 (1994)). Thus, after bisulphite treatment, DNA containing 5-methyl cytosine bases will be different in sequence from the corresponding unmethylated DNA. Primers may be chosen to amplify non-selectively a region of the genome of interest to determine its methylation status, or may be designed to selectively amplify sequences in which particular cytosines were methylated (Herman J G, Graff J R, Myohanen S, Nelkin B D and Baylin S B. Methylation-specific PCR: a novel PCR assay for methylation status of CpG islands. PNAS 93:9821-9826 (1996)).

Alternative methods for detection of cytosine methylation include digestion with restriction enzymes whose cutting is either blocked or not blocked by site-specific DNA methylation, followed by Southern blotting and hybridisation probing for the region of interest. This approach is limited to circumstances where a significant proportion (generally >10%) of the DNA is methylated at the site and where there is sufficient DNA, about 1 to 5 µg, to allow for detection. Digestion with restriction enzymes whose cutting is blocked by site-specific DNA methylation is followed by PCR amplification using primers that flank the restriction enzyme site(s). This method can utilise smaller amounts of DNA but any lack of complete enzyme digestion for reasons other than DNA methylation can lead to false positive signals.

The present inventor has now developed methods utilizing intercalating nucleic acids (INAs) suitable for the sensitive and specific detection of methylated nucleic acids which can greatly reduce the problems associated with methylation specific PCR (MSP) reaction. An unexpected property of INAs is utilized to carry out the present invention.

DISCLOSURE OF INVENTION

In a first aspect, the present invention provides an amplification blocker comprising an intercalating nucleic acid (INA) containing two or more internal intercalating pseudonucleotides (IPNs) capable of blocking or reducing nucleic acid amplification.

Preferably, the INA is about 15 to 50, more preferably about 18 to 35 nucleotides or nucleotide analogues in length having between 2 to 10, preferably between 2 to 6, internally located IPNs. It will be appreciated, however, that even longer INAs with even greater than 10 IPNs could be used. It has been found by the present inventor that IPNs situated 2 or more bases from the 3' or 5' end of an oligonucleotide provide good blocking activity for DNA polymerases. Unlike other inhibiting strategies, such as the addition of 3 prime-dideoxy bases added to oligonucleotides to stop extension, blockers according to the present invention do not require 3' or 5' positioning of chemical entities to function.

Preferably, the INA contains no IPNs at either the 3' or 5' end of the oligonucleotide.

The IPN is preferably selected from phosphoramidites of 1-(4,4'-dimethoxytriphenylmethyloxy)-3-pyrenemethyloxy-2-propanol. Preferably, the intercalator pseudonucleotide is selected from the phosphoramidite of (S)-1-(4,4'-dimethoxytriphenylmethyloxy)-3-pyrenemethyloxy-2-propanol or the phosphoramidite of (R)-1-(4,4'-dimethoxytriphenylmethyloxy)-3-pyrenemethyloxy-2-propanol. More preferably, the IPN is the phosphoramidite of (S)-1-(4,4'-dimethoxytriphenylmethyloxy)-3-pyrenemethyloxy-2-propanol.

An example of an IPN used for the examples in the present invention was the phosphoramidite of (S)-1-(4,4'-dimethoxytriphenylmethyloxy)-3-pyrenemethyloxy-2-propanol. It will be appreciated, however, that other chemical forms of IPNs can also be used.

The blockers according to the present invention are suitable for use in any form of amplification such as PCR and isothermal amplification methods. As PCR is the preferred method currently used by the health science industry, the present inventor has provided examples of the invention using PCR. It will be appreciated, however, that the invention is not restricted to PCR or any other form of amplification.

In a second aspect, the present invention provides use of a blocker according to the first aspect of the present invention to block or reduce nucleic acid amplification.

In a third aspect, the present invention provides a method for detecting the methylation status of a target region of a nucleic acid molecule comprising:
treating the nucleic acid molecule with an agent which modifies cytosine bases but does not modify 5-methyl-cytosine bases under conditions to form a modified nucleic acid template;
providing a first blocker according to the first aspect of the present invention to an amplification reaction, the first blocker being complementary to the unmethylated target region on a first strand of the modified nucleic acid template;
providing a second blocker according to the first aspect of the present invention to the amplification reaction, the second blocker being complementary to a region on the complementary second strand downstream of the first strand of the modified nucleic acid template;
providing a first primer complementary to nucleic acid region upstream from the target region on the first strand of the modified nucleic acid template;
providing a second primer complementary to nucleic acid region downstream from the second blocker region on the complementary second strand of the first strand of the modified nucleic acid template; and
carrying out a amplification reaction, wherein if the target region is methylated there will be an amplification product and if the target region is unmethylated there will be no amplification product.

In a fourth aspect, the present invention provides a method for detecting the methylation status of a target region of a nucleic acid molecule comprising:
treating the nucleic acid molecule with an agent which modifies cytosine bases but does not modify 5-methyl-cytosine bases under conditions to form a modified nucleic acid template;
providing a first blocker according to the first aspect of the present invention to an amplification reaction, the first blocker being complementary to the methylated target region on a first strand of the modified nucleic acid template;
providing a second blocker according to any according to the first aspect of the present invention to the amplification reaction, the second blocker being complementary to a region on the complementary second strand downstream of the first strand of the modified nucleic acid template;
providing a first primer complementary to nucleic acid region upstream from the target region on the first strand of the modified nucleic acid template;
providing a second primer complementary to nucleic acid region downstream from the second blocker region on the complementary second strand of the first strand of the modified nucleic acid template;
carrying out a polymerase amplification reaction, wherein if the target region is unmethylated there will be an amplification product and if the target region is methylated there will be no amplification product.

In a preferred from, the method further comprises:
providing third and fourth blockers according to the first aspect of the present invention to the amplification reaction, the third and fourth blockers being complementary to regions internal to the first and second blocker regions; and
providing third and fourth primers complementary to regions external to the third and fourth blocker regions and internal to the first and second primer regions.

In another preferred from, the method further comprises:
providing one or more additional blockers according to the first aspect of the present invention directed to one or more regions on the nucleic acid molecule.

Preferably, the regions on the nucleic acid molecule correspond to one or more regions on the modified nucleic acid template.

The method may further comprise:
providing three or more blockers according to the first aspect of the present invention directed to the first or second strands complementary to regions between the first and second primer regions.

In a fifth aspect, the present invention provides a method for detecting a conversion status of a target region of a nucleic acid molecule comprising:
treating the nucleic acid molecule with an agent which modifies cytosine bases but does not modify 5-methyl-cytosine bases under conditions to form a modified nucleic acid template;
providing a first blocker according to the first aspect of the present invention to an amplification reaction, the first blocker being complementary to the unconverted target region on a first strand of the nucleic acid molecule;
providing a second blocker according to the first aspect of the present invention to the amplification reaction, the second blocker being complementary to a region on the complementary second strand downstream of the first strand of the modified nucleic acid template;

providing a first primer complementary to nucleic acid region upstream from the target region on the first strand of the modified nucleic acid template;

providing a second primer complementary to nucleic acid region downstream from the second blocker region on the complementary second strand of the first strand of the modified nucleic acid template; and carrying out an amplification reaction, wherein if the target region is converted there will be an amplification product and if the target region is unconverted there will be no amplification product.

In a sixth aspect, the present invention provides a method for detecting a conversion status of a target region of a nucleic acid molecule comprising:

treating the nucleic acid molecule with an agent which modifies cytosine bases but does not modify 5-methyl-cytosine bases under conditions to form a modified nucleic acid template;

providing a first blocker according to the first aspect of the present invention to an amplification reaction, the first blocker being complementary to the converted target region on a first strand of the nucleic acid molecule;

providing a second blocker according to the first aspect of the present invention to the amplification reaction, the second blocker being complementary to a region on the complementary second strand downstream of the first strand of the modified nucleic acid template;

providing a first primer complementary to nucleic acid region upstream from the target region on the first strand of the modified nucleic acid template;

providing a second primer complementary to nucleic acid region downstream from the second blocker region on the complementary second strand of the first strand of the modified nucleic acid template;

carrying out an amplification reaction, wherein if the target region is unconverted there will be an amplification product and if the target region is converted there will be no amplification product.

In a seventh aspect, the present invention provides a method for detecting a status of a target region of a nucleic acid molecule comprising:

treating the nucleic acid molecule with an agent which modifies cytosine bases but does not modify 5-methyl-cytosine bases under conditions to form a modified nucleic acid template;

providing a first blocker according to the first aspect of the present invention to an amplification reaction, the first blocker being complementary to a target region on a first strand of the modified nucleic acid template having an undesired status;

providing a second blocker according to the first aspect of the present invention to the amplification reaction, the second blocker being complementary to a region on the complementary second strand downstream of the first strand of the modified nucleic acid template;

providing a first primer complementary to nucleic acid region upstream from the target region on the first strand of the modified nucleic acid template;

providing a second primer complementary to nucleic acid region downstream from the second blocker region on the complementary second strand of the first strand of the modified nucleic acid template; and carrying out a amplification reaction, wherein if the target region has a desired status there will be an amplification product and if the target region an undesired status there will be no amplification product.

In an eighth aspect, the present invention provides a method for detecting a status of a target region of a nucleic acid molecule comprising:

treating the nucleic acid molecule with an agent which modifies cytosine bases but does not modify 5-methyl-cytosine bases under conditions to form a modified nucleic acid template;

providing a first blocker according to the first aspect of the present invention to an amplification reaction, the first blocker being complementary to a target region on a first strand of the modified nucleic acid template having a desired status;

providing a second blocker according to the first aspect of the present invention to the amplification reaction, the second blocker being complementary to a region on the complementary second strand downstream of the first strand of the modified nucleic acid template;

providing a first primer complementary to nucleic acid region upstream from the target region on the first strand of the modified nucleic acid template;

providing a second primer complementary to nucleic acid region downstream from the second blocker region on the complementary second strand of the first strand of the modified nucleic acid template;

carrying out an amplification reaction, wherein if the target region has an undesired status there will be an amplification product and if the target region has a desired status there will be no amplification product.

Preferably, the status is methylation, mutation, or single nucleotide polymorphism.

In a ninth aspect, the present invention provides a method for blocking or reducing nucleic acid amplification comprising:

providing a blocker comprising an INA molecule containing two or more internal IPNs to a nucleic acid amplification reaction, wherein the blocker being complementary to a nucleic acid sequence of interest; and carrying out an amplification reaction such that the blocker binds to the nucleic acid sequence of interest and blocks or reduces amplification at or near the sequence of interest.

In a tenth aspect, the present invention provides a method for blocking or reducing nucleic acid amplification comprising:

providing a blocker according to the first aspect of the present invention to a nucleic acid amplification reaction, wherein the blocker being complementary to a nucleic acid sequence of interest; and carrying out an amplification reaction such that the blocker binds to the nucleic acid sequence of interest and blocks or reduces amplification at or near the sequence of interest.

In a preferred form, the amplification assay is polymerase amplification in the form of PCR.

The nucleic acid molecule can be DNA or RNA. Preferably, the nucleic acid molecule is DNA.

In one preferred form, the methylation status is methylated.

In another preferred form, the methylation status is unmethylated.

Preferably, the potential methylation site is cytosine (C) flanked 3' by a guanine (G), termed in the art as CpG doublet.

The modifying agent is preferably selected from bisulfite, acetate or citrate. More preferably, the agent is sodium bisulfite, a reagent, which in the presence of water, modifies cytosine into uracil.

Sodium bisulfite ($NaHSO_3$) reacts readily with the 5,6-double bond of cytosine to form a sulfonated cytosine reaction intermediate which is susceptible to deamination, and in the presence of water gives rise to a uracil sulfite. If necessary, the sulfite group can be removed under mild alkaline conditions, resulting in the formation of uracil. Thus, potentially all cytosines will be converted to uracils. Any methylated cytosines, however, cannot be converted by the modifying reagent due to protection by methylation.

In one preferred form, one or more blockers are directed to one or more potential methylation sites on the nucleic acid molecule.

In another preferred form, the blockers do not bind to potential methylation sites on the nucleic acid molecule.

In a more general form, the present inventor has found that a polymerase can be blocked from moving along a stretch of DNA by hybridizing a probe/blocker to a region of the DNA. This causes suppression of amplification of certain sequences in PCR (Saiki et al, (1998) Primer-directed enzymatic amplification Of DNA with a thermostable DNA polymerase. Science 239: 487-491. or other amplification processes such as, but not limited to, Ligase Chain Reaction (LCR, Barany F. (1991) Genetic disease detection and DNA amplification using cloned thermostable ligase. Proc. Natl. Acad. Sci. USA 88: 189-193 and isothermal methods of amplification including Strand Displacement amplification (SDA, Walker et al, (1992) Isothermal in vitro amplification of DNA by a restriction/DNA polymerase system. Proc. Natl. Acad. Sci. USA 89: 392-396, Nucleic Acid Sequence Based Amplification (NASBA, Kievitis et al, (1991) NASBA™ isothermal enzymatic in vitro nucleic acid amplification optimised for the diagnosis of HIV-1. J. Virol. Methods 35: 273-286, Transcription Based Amplification (TAS) Kwoh et al (1989) Transcription-based amplification system and detection of amplified human immunodeficiency virus type 1 with a bead-based sandwich hybridization format. Proc Natl Acad Sci USA. 4:1173-7, Helicase Chain Reaction (HCR, Vincent and Kong, (2004) Helicase-dependent isothermal DNA amplification. EMBO Reports 5(8): 1-6 Rolling Circle Amplification (RCA, Fire A. and Xu S. Q., (1995) Rolling replication of short DNA circles. Proc. Natl. Acad. Sci. USA 92: 4641-4645 Self Sustained Sequence Replication (3SR, Guatelli et al, (1990) Isothermal, in viro amplification of nucleic acids by a multienzyme reaction modelled after retroviral replication. Proc. Natl. Acad. Sci. USA 87: 1874-1878. Using modified 3' oligonucleotide sequences such as the addition of 3' dideoxynucleotides has been shown to stop polymerase extension. Unexpectedly, it has been found that the IPN molecules do not have to be placed at the terminal 3' end of the oligonucleotide but can in fact be internally placed in the INA and still block the extension of the polymerase.

It transpires that a DNA polymerase has great difficulty displacing/degrading an INA primer that has hybridized to a given genomic region, if that INA primer has multiple IPNs located within it. The IPNs in an INA effectively act as blockers to the progress of a polymerase. This unexpected property of INAs means that one can block unmethylated sequences in a region from being amplified and only amplify methylated sequences. In addition, unlike other methods to prevent polymerase extension such as the 3' terminal addition of a dideoxy-nucleotide, the present inventor has found that the IPN molecule can be placed internally and does not have to be 3' to produce the blocking effect. Thus in a mixed population of methylated and unmethylated sequences, one can remove all the background.

The present invention is also applicable for 'real-time' detection assays.

In its simplest form, the present invention relates to the use of INA blockers to differentially amplify any desired region of the human or animal or plant or microbial genome that exists in a minimum of two states. These two states are alternatives at the same genomic locus, but at the level of human or animal or plant or microbial samples are usually embedded in a mixed population of cells in which there is a particular genomic state in one population and a different genomic state in another. By the 'needle in a haystack' analogy, the invention allows for the amplification of the needle, and the blockage, of amplification for all the hay that constitutes the haystack.

In practical molecular terms this means the following: if the needle is a particular methylated genomic sequence that occurs in a cancerous cell, whereas the normal cells have an unmethylated sequence at the same locus, then the invention allows for the amplification and visualization of the methylated sequence by blocking amplification of the unwanted unmethylated sequence. The converse also applies. If the normal cells have a methylated genomic sequence, and the cancerous cells have an unmethylated sequence, then the invention also allows for the amplification and visualization of the unmethylated sequence by the blocking of the methylated sequence.

The beauty of the invention is that it allows for the detection of low level entities in a huge sea of unwanted entities. In the parlance of signal to noise ratios, in disease it is often the case of having a few cancerous cells (signal) amongst thousands of normal cells (the noise). The blocker technology according to the present invention does two things; it suppresses the noise and in addition amplifies the signal from the genomes of these two types of cells.

Although the inventor has presented data for five genes shown in the examples below, the invention is general and applicable to any part of the human or animal or plant or microbial genome, be it coding or noncoding, when that part of the genome exists in one of two states. Although the invention can be used for any situation such as detection of SNPs and genetic mutations, it has very useful application in looking for methylation status of genomic targets.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this specification.

In order that the present invention may be more clearly understood, preferred embodiments will be described with reference to the following drawings and examples.

BRIEF DESCRIPTION OF THE DRAWINGS

FIG. 2 shows illustrative details of how the INA blocker strategy works providing an overview of the location of primers and blockers used in two rounds of DNA amplification involving methylated or unmethylated DNA sequences. As this example this has been used for illustrative purposes, the blocker and primer sequences would not generally be used in a real assay. Genomic DNA sequence (SEQ ID NO 17); Bisulphite treated Methylated sequence (SEQ ID NO 18); Bisulphite treated Unmethylated sequence (SEQ ID NO 19); PCR Primer#2 (SEQ ID NO 20); PCR Primer#1 (SEQ ID NO 21); Methyl Blocker#2 (SEQ ID NO 22); Methyl Blocker#1 (SEQ ID NO 23); Unmethyl Blocker#2 (SEQ ID NO 24); Unmethyl Blocker#1 (SEQ ID NO 25).

FIG. 3 is an illustration showing the hybridisation of PCR primers and methylated INA blockers to various bisulphite treated DNA types. A. Unconverted sequence (SEQ ID NO 26); B. Bisulphite treated Methylated sequence (SEQ ID NO 27); C. Bisulphite treated Unmethylated sequence (SEQ ID NO 28); D. Regional non-converted sequence (SEQ ID NO 29); PCR Primer#1 (SEQ ID NO 30); Methyl blocker#1 (SEQ ID NO 31).

FIG. 4 is an illustration showing the hybridisation of PCR primers and unmethylated INA blockers to various bisulphite treated DNA types. A. Unconverted sequence (SEQ ID NO 26); B. Bisulphite treated Methylated sequence (SEQ ID NO 27); C. Bisulphite treated Unmethylated sequence (SEQ ID NO 28); D. Regional non-converted sequence (SEQ ID NO 29); PCR Primer#1 (SEQ ID NO 30); Unmethyl blocker#1 (SEQ ID NO 32).

FIG. 5 is an illustration showing the hybridisation of PCR primers and non-converted INA blockers to various bisulphite treated DNA types. A. Unconverted sequence (SEQ ID NO 26); B. Bisulphite treated Methylated sequence (SEQ ID NO 27); C. Bisulphite treated Unmethylated sequence (SEQ ID NO 28); D. Regional non-converted sequence (SEQ ID NO 29); PCR Primer#1 (SEQ ID NO 30); non converted blocker#1 (SEQ ID NO 33).

FIG. 7 shows data on the application of the INA blocker technology to bisulphite treated genomic DNA samples. INA blockers and PCR primers for the GSTP1 promoter region have been applied to nine genomic DNA samples (described in Table 3) to evaluate the methylation status of the promoter region.

MODE(S) FOR CARRYING OUT THE INVENTION

Materials and Methods

INA/IPN Definition

Figure 1:
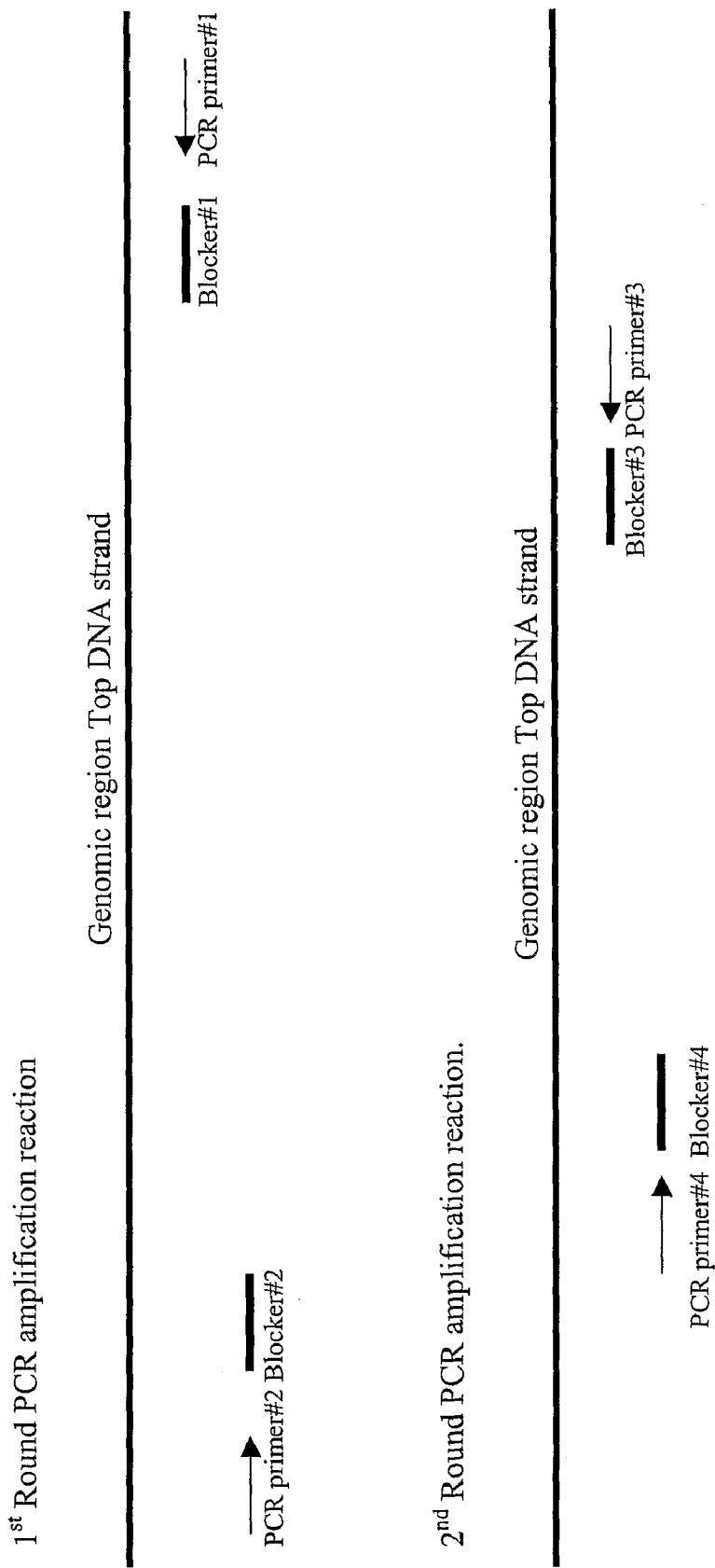
FIG. 1 shows illustrative details of the INA blocker strategy providing an overview of the location of primers and blockers used in two rounds of DNA amplification.

Intercalating Nucleic Acids (INAs) are a unique class of DNA binding molecules. INAs are comprised of nucleotides and/or nucleotide analogues and intercalating pseudonucleotide (IPN) monomers. INAs have a very high affinity for complementary DNA with stabilisations of up to 10 degrees for internally placed IPNs and up to 11 degrees for end position IPNs. The INA itself is a selective molecule that prefers to hybridise with DNA over complementary RNA. It has been shown that INAs bind about 25 times less efficiently to RNA than oligonucleotide primers. Whereas, conventional oligonucleotides, oligonucleotide analogues and PNAs have an equal affinity for both RNA and DNA. Thus INAs are the first truly selective DNA binding agents. In addition, INAs have a higher specificity and affinity for complementary DNA that other natural DNA molecules.

In addition, IPNs stabilise DNA best in AT-rich surroundings which make them especially useful in the field of epigenomics research. The IPNs are typically placed as bulge or end insertions in to the INA molecule. The IPN is essentially a planar (hetero) polyaromatic compound that is capable of co-stacking with nucleobases in a nucleic acid duplex.

The INA molecule has also been shown to be resistant to exonuclease attack. This makes these molecules especially useful as primers for amplification using enzymes such as phi29. As phi29 has inherent exonuclease activity, primers used as templates for amplification must be specially modified at their 3' terminus to prevent enzyme degradation. INA molecules, however, can be added without further modification.

INAs can be used in conventional PCR amplification reactions and behave as conventional primers. INAs, however, have a higher specificity for the DNA template making them ideal for the use in situations where template is limiting and sensitivity of the reaction is critical. INAs stabilise DNA best in AT-rich surroundings which make them especially useful for amplification of bisulphite treated DNA sequences. This is due to the fact that after bisulphite conversion, all the cytosine residues are converted to uracil and subsequently thymine after PCR or other amplification. Bisulphite treated DNA is therefore very T rich. Increasing the number of IPN molecules in the INA results in increased stabilization of the INA/DNA duplex. The more IPNs in the INA, the greater the melting temperature of the DNA/INA duplex. Unexpectedly, when multiple IPNs were positioned in the nucleotide molecule, although the INA has a very high specificity for its complementary DNA, the inclusion of the IPNs resulted in the inhibition of PCR polymerase extension in the amplification reaction. Thus if INAs are designed with multiple IPNs, they act as blocking reagents in the PCR amplification reaction which does not occur using conventional oligonucleotides.

The present applicant has previously developed a class of intercalator pseudonucleotides which, when incorporated into an oligonuceotide or oligonuceotide analogue, form an intercalating nucleic acid (INA) (WO 03/051901, WO 03/052132, WO 03/052133 and WO 03/052134, incorporated herein by reference) which has novel and useful properties as a supplement to, or replacement of, oligonucleotides. It has now been found that oligonucleotides or oligonucleotide analogues can be modified to include one or more intercalator pseudonucleotides (IPN) to form a blocker of nucleic acid amplification.

The intercalator pseudonucleotide is preferably selected from phosphoramidites of 1-(4,4'-dimethoxytriphenylmethyloxy)-3-pyrenemethyloxy-2-propanol. Preferably, the intercalator pseudonucleotide is selected from the phosphoramidite of (S)-1-(4,4'-dimethoxytriphenylmethyloxy)-3-pyrenemethyloxy-2-propanol or the phosphoramidite of (R)-1-(4,4'-dimethoxytriphenylmethyloxy)-3-pyrenemethyloxy-2-propanol.

The oligonucleotide or oligonucleotide analogue can be selected from DNA, RNA, locked nucleic acid (LNA), peptide nucleic acid (PNA), MNA, altritol nucleic acid (ANA), hexitol nucleic acid (HNA), intercalating nucleic acid (INA), cyclohexanyl nucleic acid (CNA) and mixtures thereof and hybrids thereof, as well as phosphorous atom modifications thereof, such as but not limited to phosphorothioates, methyl phospholates, phosphoramidites, phosphorodithiates, phosphoroselenoates, phosphotriesters and phosphoboranoates. Non-naturally occurring nucleotides include, but not limited to the nucleotides comprised within DNA, RNA, PNA, INA, HNA, MNA, ANA, LNA, CNA, CeNA, TNA, (2'-NH)-TNA, (3'-NH)-TNA, α-L-Ribo-LNA, α-L-Xylo-LNA, β-D-Xylo-LNA, α-D-Ribo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo[4.3.0]-DNA, Bicyclo[3.2.1]-DNA, Bicyclo[4.3.0]amide-DNA, β-D-Ribopyranosyl-NA, α-L-Lyxopyranosyl-NA, 2'-R-RNA, α-L-RNA or α-D-RNA, β-D-RNA. In addition non-phosphorous containing compounds may be used for linking to nucleotides such as but not limited to methyliminomethyl, formacetate, thioformacetate and linking groups comprising amides. In particular nucleic acids and nucleic acid analogues may comprise one or more intercalator pseudonucleotides.

Preferably, the blockers are DNA oligonucleotides containing two or more internal IPNs forming blocking INAs.

When IPNs are placed in an INA molecule for the specific detection of methylated sites, the present inventor has found that it is useful to avoid placing an IPN between potential CpG sites. This is due to the fact that when a CpG site is split using an IPN the specificity of the resulting INA is reduced.

Genomic Nucleic Acid

Genomic nucleic acid can be DNA or RNA obtained from plants, animals, microorganisms such as bacteria, fungi, yeasts and viruses. Preferably, the nucleic acid is DNA, more preferably genomic DNA from an animal or human, or nucleic acid of an infectious agent of animal or human cells.

Bisulphite Treatment of DNA

An exemplary protocol for effective bisulphite treatment of nucleic acid is set out below. The protocol results in retaining substantially all DNA treated. This method is also referred to herein as the Human Genetic Signatures (HGS) method. It will be appreciated that the volumes or amounts of sample or reagents can be varied.

Preferred method for bisulphite treatment can be found in U.S. Ser. No. 10/428,310 or PCT/AU2004/000549 incorporated herein by reference.

To 2 µg of DNA, which can be pre-digested with suitable restriction enzymes if so desired, 2 µl (1/10 volume) of 3 M NaOH (6 g in 50 ml water, freshly made) was added in a final volume of 20 µl. This step denatures the double stranded DNA molecules into a single stranded form, since the bisulphite reagent preferably reacts with single stranded molecules. The mixture was incubated at 37° C. for 15 minutes. Incubation at temperatures above room temperature can be used to improve the efficiency of denaturation.

After the incubation, 208 µl 2 M Sodium Metabisulphite (7.6 g in 20 ml water with 416 ml 10 N NaOH; BDH AnalaR #10356.4D; freshly made) and 12 µl of 10 mM Quinol (0.055 g in 50 ml water, BDH AnalR #103122E; freshly made) were added in succession. Quinol is a reducing agent and helps to reduce oxidation of the reagents. Other reducing agents can also be used, for example, dithiothreitol (DTT), mercaptoethanol, quinone (hydroquinone), or other suitable reducing agents. The sample was overlaid with 200 µl of mineral oil. The overlaying of mineral oil prevents evaporation and oxidation of the reagents but is not essential. The sample was then incubated overnight at 55° C. Alternatively the samples can be cycled in a thermal cycler as follows: incubate for about 4 hours or overnight as follows: Step 1, 55° C./2 hr cycled in PCR machine; Step 2, 95° C./2 min. Step 1 can be performed at any temperature from about 37° C. to about 90° C. and can vary in length from 5 minutes to 8 hours. Step 2 can be performed at any temperature from about 70° C. to about 99° C. and can vary in length from about 1 second to 60 minutes, or longer.

After the treatment with Sodium Metabisulphite, the oil was removed, and 1 µl tRNA (20 mg/ml) or 2 µl glycogen were added if the DNA concentration was low. These additives are optional and can be used to improve the yield of DNA obtained by co-precipitating with the target DNA especially when the DNA is present at low concentrations. The use of additives as carrier for more efficient precipitation of nucleic acids is generally desired when the amount nucleic acid is <0.5 µg.

An isopropanol cleanup treatment was performed as follows: 800 µl of water were added to the sample, mixed and then 1 ml isopropanol was added. The water or buffer reduces the concentration of the bisulphite salt in the reaction vessel to a level at which the salt will not precipitate along with the target nucleic acid of interest. The dilution is generally about 1/4 to 1/1000 so long as the salt concentration is diluted below a desired range, as disclosed herein.

The sample was mixed again and left at 4° C. for a minimum of 5 minutes. The sample was spun in a microfuge for 10-15 minutes and the pellet was washed 2× with 70% ETOH, vortexing each time. This washing treatment removes any residual salts that precipitated with the nucleic acids.

The pellet was allowed to dry and then resuspended in a suitable volume of T/E (10 mM Tris/0.1 mM EDTA) pH 7.0-12.5 such as 50 µl. Buffer at pH 10.5 has been found to be particularly effective. The sample was incubated at 37° C. to 95° C. for 1 min to 96 hr, as needed to suspend the nucleic acids.

Blocker Production

A suitable method for the production of INA blockers can be found in Christensen U B, Pedersen E B. Intercalating nucleic acids containing insertions of 1-O-(1-pyrenylmethyl) glycerol: stabilisation of dsDNA and discrimination of DNA over RNA. Nucleic Acids Res. 2002 Nov. 15; 30(22):4918-25, incorporated herein by reference.

Blockers

As defined herein, a 'blocker' is an intercalating nucleic acid (INA) containing two or more internal intercalating pseudonucleotides (IPNs) capable of blocking or reducing nucleic acid amplification.

As defined herein, a 'methyl blocker' is blocker designed to target a region of converted nucleic acid that was originally methylated in its untreated genomic state. As defined herein, an 'unmethyl blocker' is blocker designed to target a region of converted nucleic acid that was not methylated in its untreated genomic state.

As defined herein, a 'converted blocker' is blocker designed to target a region of converted nucleic acid.

As defined herein, an 'unconverted blocker' is blocker designed to target a region of genomic nucleic acid (ie unconverted by bisulfite or other treatment).

Examples of INA blockers used in the illustrative example for the GSTP1 gene are as follows:

```
MB-1   5' TYT TCG GTT AGY TTG CGC GGC GAY TTT CGG YGG A   (SEQ ID NO 1)

UB-1   5' TYT TTG GTT AGY TTG TGT GGT GAY TTT TGG YGG A   (SEQ ID NO 2)

NCB-1  5' CYC CCG GCC AGY CTG CGC GGC GAY CTC CGG YGG A   (SEQ ID NO 3)
```

```
MB-2    5' TTA YTA ACG AAA YAC TYA CGA CGA CGA AAC YTC C   (SEQ ID NO 4)

UB-2    5' TTA YTA ACA AAA YAC TYA CAA CAA CAA AAC YTC C   (SEQ ID NO 5)

NCB-2   5' TGG YTG GCG AAG YAC TYG CGG CGG CGA AAC YTC C   (SEQ ID NO 6)

MB-3    5' TTY AGG GCG TYT TTT TYT GCG GTC GAC GTY T       (SEQ ID NO 7)

UB-3    5' TTY AGG GTG TYT TTT TYT GTG GTT GAT GTY T       (SEQ ID NO 8)

NCB-3   5' CCY AGG GCG CYC CCT CYT GCG GCC GAC GCY C       (SEQ ID NO 9)

MB-4    5' ATY AAT CCC GCC YCC GCT YCC GCC CCA YAT A       (SEQ ID NO 10)

UB-4    5' ATY AAT CCC ACC YCC ACT YCC ACC CCA YAT A       (SEQ ID NO 11)

NCB-4   5' GTY GGT CCC GCC YCC GCT YCC GCC CCA YGT G       (SEQ ID NO 12)
``` wherein Y designates an IPN. Preferably, the IPN is in the form of the phosphoramidite of (S)-1-(4,4'-dimethoxytriphenylmethyloxy)-3-pyrenemethyloxy-2-propanol.
MB is a Methylated Blocker
UB is an Unmethylated blocker
NCB is an Non-converted blocker
The descriptor 'Y' denotes the placement of the IPN in the sequence, and is included in the base count of the sequence.
PCR Primers
Primers used for illustration were as follows:

```
GSTP1-1   TTT GTT GTT TGT TTA TTT TTT AGG TTT   (SEQ ID NO 13)

GSTP1-2   AAC CTA ATA CTA CTA ATT AAC CCC AT    (SEQ ID NO 14)

GSTP1-3   GGA TTT GGG AAA GAG GGA AAG GTT TT    (SEQ ID NO 15)

GSTP1-4   ACT AAA AAC TCT AAA CCC CAT CCC       (SEQ ID NO 16)
```

1st round INA blocking PCR
GSTP1-1/2+appropriate Blocker 1/2
$2^{nd}$ round INA blocking PCR
GSTP1-3/4+appropriate Blocker 3/4.

Conventional Bisulphite Modification of DNA and Visualization of a Product for a Given Genomic Region This involves treatment of a DNA sample with bisulphite followed by a PCR amplification step. The product of the PCR step, say the visualization of a band on a gel, does not tell the researcher if the DNA was methylated or not at this stage, only that there was bisulphite treated DNA for that particular gene region present in the sample. After PCR and visualization, the product still needs to be either digested by restriction enzymes to see if a particular site is cut by the enzyme or not, (and hence whether it was methylated or not), or the DNA band or fragment needs to be sequenced to determine if the gene region was methylated, or not, in that particular tissue sample. Sequencing a PCR band will reveal whether each C in a CpG doublet for example in that region was methylated or not. This method lacks sensitivity as methylation will only be confidently and routinely detected on a sequencing apparatus if greater than 10% of the sample was methylated. In a particular tissue sample, for example, if 90% of the cells in that sample had unmethylated DNA in the region under study and 10% had methylated DNA, the conventional method described above would lack the sensitivity for the accurate determination of methylation profiling. Furthermore, this prior art method is very labour intensive and time consuming to perform.

Methylation Specific PCR (MSP)

Although MSP has been widely adopted by the methylation research community, MSP has a number of very serious limitations or drawbacks that are documented in the literature. These limitations or drawbacks include:

I. The method is very prone to false positive signals especially if there are small numbers of cancerous cells with methylated DNA regions in a mixed population of normal and cancerous cells, as is the case with most cancerous tissues due to the heterogeneity of the tumour. For ease of illustration the normal cells have their equivalent regions in an unmethylated state. The false positive signals arise as a result of regional non-conversion of the DNA when treated with bisulphite. Thus PCR primers amplify non-converted regions (see FIGS. 3, 4 and 5 region D) of the DNA and so one obtains what one believes to be a methylated answer, but in fact it's a gene region that has simply failed to be converted by the bisulphite treatment. INA blockers do not suffer from this problem as it is possible to include non-converted INA blockers which will block the amplification of non-converted DNA regions. If a positive signal is obtained using INA blocker technology, the signal will be the result of fully converted DNA. Thus. false positive PCR signals are eliminated using the blockers according to the present invention.

II. Unless the region has been previously sequenced after conventional bisulphite treatment (not a sensitive approach), the researcher does not know if the CpG site which is being targeted was methylated in the first place. Thus a certain CpG site may be unmethylated or under methylated and unless the region had been sequenced, a MSP primer designed against that particular CpG would either produce a false negative reaction or under estimate the degree of methylation of that particular gene. Again the INA blocker technology according to the present invention overcomes this limitation as the PCR primers can be designed to regions that do not contain CpG dinucleotides. Thus the PCR primers will bind whether the gene is methylated or not.

III. If the sequence contains only a small area of methylation, for example in the 1$^{st}$ part of the sequence and this does not extend the full length of the sequence, then this would yield a false negative result with MSP. This is due to the fact that although the 1$^{st}$ MSP primer will bind to the complementary CpG site the second MSP primer will not bind as the second region was unmethylated. The blockers do not have this problem as already stated above as the PCR primers can be designed to regions that will amplify regardless of whether they were methylated or not.

IV. MSP is very difficult to optimise as the reaction relies on the ability of the PCR enzyme to prime off the 3' terminal base which is either a methylated C or an unmethylated T base. Thus, different MSP reactions for different gene regions may have very different hybridisation temperatures between the MSP primer and the converted target region (Tm optima). If one gene region contains a very dense CpG island and the other gene region has much fewer CpG's, then the gene region from the CpG island might have a Tm of 70° C. while the other gene region might have a Tm of 50° C. Therefore, if an MSP reaction is performed at high stringency, the gene with Tm of 70° C. will produce a PCR product, while the MSP reaction with the Tm of 50° C. will produce no amplified product. Thus, it would be close to impossible to carry out multiple MSP reactions (each in a different well in the same plate 96 well or 384 well PCR plate) and get sensible results out the other end as each well will have different Tm optima and amplification or not will vary in an unpredictable manner. Again as the PCR primers in the blocker technology according to the present invention can be designed against regions of genes that are devoid of CpGs, the Tm optima of multiple different genes is much more easy to control as even in relatively dense CpG islands. It is usually possible to find a small region within that island that is devoid of CpG dinucleotides that will serve as a priming site for a PCR primer.

V. MSP only detects the presence of methylation at one specific CpG site per primer, so the MSP reaction only ever reports on two sites per gene region. This has always been a well documented criticism. It does not tell the researcher anything about the methylation state of the area between the PCR primers. The blocker INAs can contain on average 3-4 CpG sites thus using 4 blockers per gene the present invention can be used to interrogate on average from 12-16 CpG sites for methylation status.

Results

Blocker Strategy

The present invention is first illustrated by the following an amplification assay.

In FIG. 1, PCR primer#1 and blocker #1 hybridises to bisulphite treated DNA from the genomic region of interest. Taq polymerase then extends from PCR primer#1 until it reaches blocker#1 bound to the top DNA strand at which point the enzyme stops. If for some reason the enzyme does bypass blocker#1, the enzyme will copy the top strand of the DNA and produce the complementary strand creating the binding site for PCR primer#2. Therefore, a second blocker complementary to a sequence internal of PCR#2 is added. This then ensures that no amplification of genomic region.

Due to the nature of bisulphite treated DNA, amplification efficiency, particularly by PCR, is reduced as the DNA is now essentially composed of a 3 base genome. Therefore for maximum sensitivity, a second round of PCR can be performed. The second round PCR improves the sensitivity of the reaction at least five orders of magnitude, thus making the method ideal for the detection of DNA methylation changes that occur in a small subpopulation of cells, such as the very low numbers of cancer cells in a mixed population of cancerous and normal cells in a clinical sample. In this regard, a third and a fourth PCR primer (PCR primer#3 and PCR primer#4) internal to PCR primer#1 and primer#2 are added along with two further blockers (blocker#3 and blocker#4). Thus each PCR primer has a blocker sequence that is complementary to a sequence internal of that PCR primer.

Therefore, for each genomic region of interest, a total of four PCR primers are synthesised. If detection of the presence of methylated DNA sequences was required, four unmethylated blocking sequences would be used to block the amplification of unmethylated DNA. In addition, to ensure that the sequence had been fully converted by the bisulphite treatment (a potential problem associated with some bisulphite treatment reactions) a further four non-converted sequences could be used to block the amplification of regions of DNA that have undergone only partial conversion. In this regard, in each PCR (or other amplification) reaction there would be two PCR primers, 2 unmethylated blockers and 2 non-converted blockers.

Conversely, if detection of the presence of unmethylated DNA sequences was required, four methylated blocking sequences could be used to block the amplification of methylated DNA. In addition, to ensure that the sequence had been fully converted by the bisulphite treatment a further four non-converted sequences could be used to block the amplification of regions of DNA that have undergone only partial conversion. Again, in each PCR reaction there would be two PCR primers, 2 methylated blockers and 2 non-converted blockers.

It will be appreciated that the blockers can be used to block any amplification of nucleic acid.

Blocker Specific Amplification

FIG. 2 shows normal and bisulphite treated artificial DNA sequences for demonstration purposes, PCR primer#1 and primer#2 targeting non-CpG containing regions and the sequences of the four blocker sequences (two methylated and two unmethylated) which hybridise to their appropriate target region.

Hybridisation of PCR Primers and INA Blockers to Unconverted DNA (Wild Type)

In FIG. 3, the PCR primer#1 will only hybridise to B, C and D, not the unconverted sequence A due to insufficient sequence similarity. The methyl-blocker will only bind to the bisulphite treated methylated sequence B, but not to the unconverted, unmethylated or regionally non-converted DNA sequences again due to insufficient sequence similarity. Taq polymerase will then begin extending the sequences shown in B, C and D. However, in case B the enzyme will come to the methyl blocker but will not be able to pass the methyl-blocker thus no product will be formed. In case C no blocker has bound due to mismatch bases at the TpG sites, so Taq will produce the desired PCR fragment. In case D again no blocker has bound due to insufficient sequence similarity therefore a PCR product will be obtained but this product will contain non-converted sequences.

Hybridisation of PCR Primers and Blockers to Converted Methylated DNA Sequences

In FIG. 4, the PCR primer#1 will only hybridise to B, C and D, not the unconverted sequence A due to insufficient sequence similarity. The unmethyl-blocker will only bind to the bisulphite treated unmethylated sequence C, not to the unconverted, methylated or regional unconverted DNA sequences again due to insufficient sequence similarity. Taq polymerase will then begin extending the sequences shown in B, C and D. In case C the enzyme will come to the unmethyl blocker but will not be able to pass the unmethyl-blocker thus no product will be formed. In case B no blocker has bound due to mismatched bases at the CpG, so Taq will produce the desired PCR fragment. In case D again no blocker has bound due to insufficient sequence similarity, therefore a PCR product will be obtained but this product will contain non-converted sequences.

Hybridisation of PCR Primers and Blockers to Regionally Non-converted DNA Sequences In FIG. 5, the PCR primer#1 will only hybridise to B, C and D, not the unconverted sequence A due to insufficient sequence similarity. The non-converted blocker will bind to the non-converted sequence A and the regionally non-converted sequence D not to the methylated or unmethylated DNA sequences again due to insufficient sequence similarity. Taq polymerase will then begin extending of the sequences shown in B, C and D. In case D the enzyme will come to the non-converted blocker but will not be able to pass the non-converted blocker thus no product will be formed. In case B and C no blocker has bound due to sequence mismatched bases at the CpG and TpG sites, so Taq will produce the desired PCR fragment.

Thus the non-converted blocker can be added to situations set out in FIG. 3 and FIG. 4 along with the appropriate blockers and primers to prevent the amplification of regionally non-converted sequences, a major problem with conventional MSP.

Comparison of Methodologies

Figure 6:
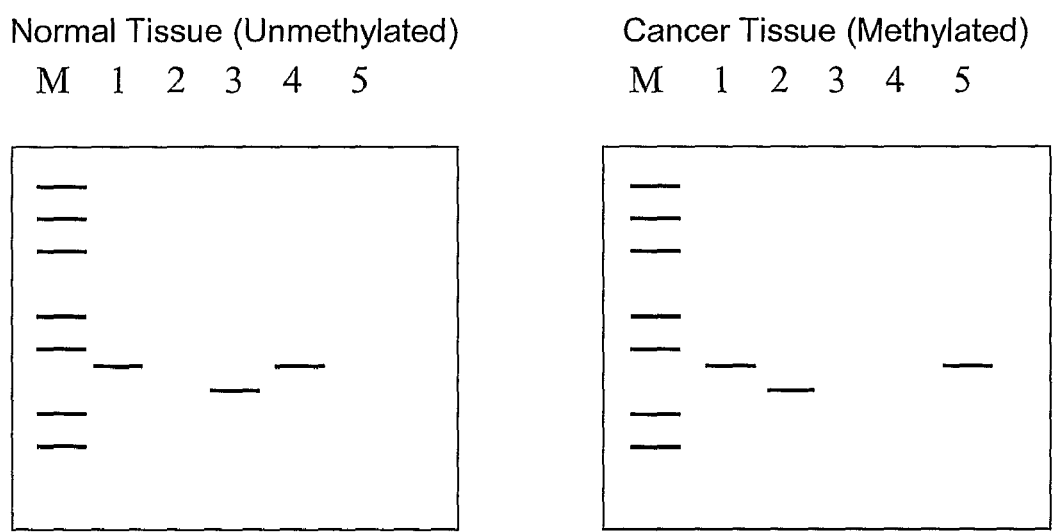
FIG. 6 shows the expected amplification products visualized on agarose gel electrophoresis using conventional PCR, MSP technology, or the INA blockers and primer combinations outlined in FIGS. 3, 4 and 5. The results are shown by illustration of the positions and sizes of the expected amplification products detected on gels using various amplification/detection methodologies relative to a defined set of known DNA markers.

FIG. 6 shows a schematic representation of the banding patterns which would be observed on an agarose gel using conventional bisulphite PCR, Methylation Specific PCR (MSP) and INA blocker technology.

With conventional bisulphite PCR a band would be seen whether or not the sample contained methylated sequences or not, normal tissue versus cancer tissue, (Lane 1 in both panels). This particular method only detects the presence of bisulphite treated DNA in the sample and has to be further processed to determine the methylation status, usually by dideoxy sequencing.

Using MSP for the detection of methylated DNA sequences, no band would be seen in Lane 2 from the normal tissue sample as the normal tissue would be unmethylated. However, a band would be seen in Lane 2 of the cancer tissue sample. Using MSP primers directed against unmethylated sequences, a band would be observed in the normal tissue sample (Lane 3) but not in the cancerous tissue sample (see Lane 3).

With INA blocker technology using methylated blockers, a band would be observed in the normal tissue (Lane 4) but not in the cancerous tissue (see Lane 4). Using unmethylated blockers a band would be observed in the cancerous tissue (Lane 5) but not in the normal tissue (see Lane 5).

Blocker Technology Applied to Bisulphite Treated Genomic DNA Samples

FIG. 7 shows that when unmethylated blockers were added to the PCR reaction mix, positive PCR signals were generated with the bisulphite converted DNA HeLa cell line, T-cells from a clinical sample and the breast cancer cell line T47D2.

TABLE 1

| Lane | Sample | Cell Type | Methylation[@] |
|---|---|---|---|
| 1 | HeLa | Cervical (cell line) | Yes |
| 2 | HuVec | Endothelial (cell line) | No |
| 3 | THP | Monocyte (cell line) | No |
| 4 | T-cell | Blood | No |
| 5 | B-cell | Blood | No |
| 6 | CD34+ | Blood | No |
| 7 | T47D2 | Breast (cell line) | Yes/No[$] |
| 8 | 500 ng placenta DNA | Placenta | No |
| 9 | 100 ng placenta DNA | Placenta | No |

[@]Methylation measured by conventional bisulphite PCR, which will only detect methylation if greater than 10% of the sample contained methylated sequences.
[$]When the T47D2 was sequenced by conventional bisulphite sequencing it was found that the first half of the sequence was methylated but the second half was not.

Purification of T-cells, B-cells and CD34+ Cells from Whole Blood

Samples were obtained from a patient undergoing leukapheresis at the Royal North Shore Hospital, Sydney, Australia. Samples were obtained with prior Ethics Committee approval. White blood cells were concentrated using Ficoll Paque plus (Amersham Biosciences #17-1440-03; Piscataway N.J.) according to the manufacturers instructions. T-cells, B-cells and CD34+ cells were isolated from the white cell population using CELLection CD2 Dynabeads (Dynal #116.03; Lake Success N.Y.), Dynabeads CD19 (Pan B) Dynal#111.43 and Dynal CD34 Progenitor Cell selection system (Dynal #113.01) respectively according to the manufactures instructions.

Sequences and primers used are set out in Table 2.
PCR premixes were prepared as follows:

|  | Unmethylated mixes | Methylated mixes | Control reaction |
|---|---|---|---|
| X2 Master mix (Promega) | 12.5 μl | 12.5 μl | 12.5 μl |
| 100 ng/μl PCR#1 | 1 μl | 1 μl | 1 μl |
| 100 ng/μl PCR#2 | 1 μl | 1 μl | 1 μl |
| 100 ng/μl Blocker#1 | 3 μl (U) | 3 μl (M) | — |
| 100 ng/μl Blocker#2 | 3 μl (U) | 3 μl (M) | — |
| Water | 3.5 μl | 3.5 μl | 9.5 μl |

TABLE 2

| NAME | SEQUENCE | SEQ ID NO | PCR PRIMER | SEQUENCE | SEQ ID NO |
|---|---|---|---|---|---|
| CDKN2B MB-1 | GAT TYT TGC GYA CGC GYT TCG TAT YTT TG | 34 | CDKN2B-1 | TTTTTGGTTTAGTTGAAAAAGGAATTT | 35 |
| CDKN2B MB-2 | GTT YAA CGA YTC GGT CGT YTC GGT TYA TTG | 36 | CDKN2B-2 | TTAGGAGTTTTTTTTAGAAGTAATTTAGG | 37 |
| CDKN2B MB-3 | CCY CGC GCC GCG YAC GCT YAA CCY AAA C | 38 | CDKN2B-3 | ACTTCCAAAAACTATGTGACCTTCTCCACTAA | 39 |
| CDKN2B MB-4 | AAC TCC GTT YAA AAY TCC GCG CCG YAC TTY C | 40 | CDKN2B-4 | AAACCCTAAAACCCCAACTACCTAA | 41 |
| CDKN2B UB-1 | GAT TYT TGT GYA TGT GYT TTG TAT YTT TG | 42 | | | |
| CDKN2B UB-2 | GTT YAA TGA YTT GGT TGT YTT GGT TYA TTG | 43 | | | |
| CDKN2B UB-3 | CCY CAC ACC ACA YAC ACT YAA CCY AAA C | 44 | | | |
| CDKN2B UB-4 | AAC TCC ATT YAA AAY TCC ACA CCA YAC TTY C | 45 | | | |
| CDK2NB-NCB1 | GAC TYC CGC GYA CGC GYT CCG CAC YCC TG | 46 | | | |
| CDK2NB-NCB2 | GCT YAA CGA YCC GGC CGC YTC GGC CYA CTG | 47 | | | |
| CDK2NB-NCB3 | CCY CGC GCC GCG YGC GCT YGG CCY AGA C | 48 | | | |
| CDK2NB-NCB4 | GAC TCC GTT YGG GAY TCC GCG CCG YGC TTY C | 49 | | | |
| CYCL-2 MB-1 | GGT TTY ACG AYA GCG TTT TYT TCG TAG YGC G | 50 | CYCL2-1 | ATTGAAATGTTTTTTAGAGAAGTAATTTT | 51 |
| CYCL-2 MB-2 | GAY GCG GCG GGT YTT TCG TYT TTC GTT TTY AG | 52 | CYCL2-2 | GTGGGTTTAAGGGATTTGATTT | 53 |
| CYCL-2 MB-3 | YCC CGA AAC TCC AYA ATC GAT CYC CGA ATY TC | 54 | CYCL2-3 | ACCCCTTTTATACATAATTAAAAC | 55 |
| CYCL-2 MB-4 | YCT AAA AYA ACC CGA AYA TCC CGA ACY C | 56 | CYCL2-4 | AACTAACAAAAAACTACCTATAACC | 57 |
| CYCL-2 UB-1 | GGT TTY ATG AYA GTG TTT TYT TTG TAG YGT G | 58 | | | |
| CYCL-2 UB-2 | GAY GTG GTG GGT YTT TTG TYT TTT GTT TYT AG | 59 | | | |
| CYCL-2 UB-3 | YCC CAA AAC TCY AAA ATC AAT CYC CAA ATY TC | 60 | | | |
| CYCL-2 UB-4 | YCT AAA AYA ACC CAA AYA TCC CAA ACY C | 61 | | | |
| CYCL2-NCB1 | GGT TCY ACG AYA GCG CCT CYC TCG CAG YGC G | 62 | | | |
| CYCL2-NCB2 | GAY GCG GCG GGC YTC TCG CYT CCC GCT CCY AG | 63 | | | |
| CYCL2-NCB3 | YCC CGG AGC TCC AYG ATC GAT CYC CGA GTY TC | 64 | | | |
| CYCL2-NCB4 | YCT GGA AYA GCC CGG AYG TCC CGG GYC C | 65 | | | |
| GSN MB-1 | GTT YGG GTT CGT CGY TCG TTC GTY GTT TYG | 66 | GSN-1 | TTGTAAAATGGGTTGGTAGTTGTATTT | 67 |
| GSN MB-2 | GTT YAG CGT YTC GTC GTA TYG TTA YGG | 68 | GSN-2 | TTGAAAAGGATGTGTTGATGTT | 69 |
| GSN MB-3 | AYT CGA CCC GYA CAA AYA CGC GAC AYA C | 70 | GSN-3 | AATCTTAAAAACATCTAAATTC | 71 |
| GSN MB-4 | YCC CGC CCA TCY CCG CCC AAY ACC GAA AYA C | 72 | GSN-4 | ACAAAAAACCCAATCTACAAC | 73 |
| GSN UB-1 | GTT YGG GTT TGT TGY TTG TTT GTY GTT TYG | 74 | | | |
| GSN UB-2 | GTT YAG TGT YTT GTT GTA TYG TTA YGG | 75 | | | |
| GSN UB-3 | AYT CAA CCC AYA CAA AYA CAC AAC AYA C | 76 | | | |
| GSN UB-4 | YCC CAC CCA TCY CCA CCC AAY ACC AAA AYA C | 77 | | | |
| GSN-NCB1 | GCT YGG GCT CGC CGY CCG CTC GTY GCC TYG | 78 | | | |
| GSN-NCB2 | GCT YAG CGC YCC GCC GTA TYG TCA YGG | 79 | | | |
| GSN-NCB3 | AYT CGA CCC GYA CAG GYG CGC GGC AYG C | 80 | | | |
| GSN-NCB4 | YCC CGC CCA TCY CCG CCC AYY GCC GGG GYA C | 81 | | | |
| HIC-1 MB-1 | GYT TTT YGG GGC GTG TYA GGT CGT TTT YGG | 82 | HIC1-1 | GGTAATTGTTTTTAAAAGGGTTAT | 83 |
| HIC-1 MB-2 | GYG TTA GGC GGT TYA GGG CGT CGT YAC GGY T | 84 | HIC1-2 | GTTTTTATTTTAGAGGGTAGTTGG | 85 |

TABLE 2-continued

| NAME | SEQUENCE | SEQ ID NO | PCR PRIMER | SEQUENCE | SEQ ID NO |
|---|---|---|---|---|---|
| HIC-1 MB-3 | TAY ACC GAY ACG CCT CCY ATC GTA TCY C | 86 | HIC1-3 | ATTAAACTAATTATCATACACCACCAAAA | 87 |
| HIC-1 MB-4 | CTT YAT ACG CGC GAY AAA AAY AAC GTY TC | 88 | HIC1-4 | ATATAAATAAAATCCAACACCAAACTAAAC | 89 |
| HIC-1 UB-1 | GYT TTT YGG GGT GTG TYA GGT TGT TTT YGG | 90 | | | |
| HIC-1 UB-2 | GYG TTA GGT GGT TYA GGG TGT TGT YAT GGY T | 91 | | | |
| HIC-1 UB-3 | TAY ACC AAY ACA CCT CCY ATC ATA TCY C | 92 | | | |
| HIC-1 UB-4 | CTT YAT ACA CAC AAY AAA AAY AAC ATY TC | 93 | | | |
| HIC1-NCB1 | GYC CCT YGG GGC GTG CYA GGC CGC CCT YGG | 94 | | | |
| HIC1-NCB2 | GYG CCA GGC GGC CYA GGG CGC CGC YAC GGY C | 95 | | | |
| HIC1-NCB3 | TGY GCC GGY GCG CCT CCY ATC GTG TYC C | 96 | | | |
| HIC1-NCB4 | CTT YGT GCG CGC GGY AAG AGY GGC GTY TC | 97 | | | |

Two rounds of PCR amplification were performed in a Hybaid PX2 thermocycler according to the principles described in FIG. 1. One μl of bisulphite treated genomic DNA was added to each of the 1$^{st}$ round PCR reaction tubes. The PCR was carried out as follows.

| 95° C. | 3 minutes | 1 cycle |
|---|---|---|
| 95° C. | 1 minute | |
| 55° C. | 2 minutes | 30 cycles |
| 72° C. | 2 minutes | |
| 72° C. | 10 minutes | 1 cycle |

After the 1$^{st}$ round PCR was complete, 1 μl of the 1$^{st}$ round PCR reaction mixture was transfered to the second round amplification tubes and the above PCR program repeated.

Ten μl of the PCR reaction mix was then resolved on a 2% agarose gel.

Conventional bisulphite genomic sequencing of these samples revealed that the HeLa cell DNA line was completely methylated for this particular genomic region. T-cell DNA showed a lack of methylation, however, the resolution of conventional bisulphite genomic sequencing is only 10%. Restriction digestion of the amplified product using the restriction enzymes Taq 1 (cuts TCGA) and BstU1 (cuts CGCG) revealed methylation in the amplicon. This shows that the INA blocker technology is clearly superior to conventional bisulphite genomic sequencing at the detection of low level methylated sequences. In addition, when the T47D2 DNA was sequenced by conventional bisulphite sequencing, it was found that the first half of the sequence was methylated but the second half was not. As can be seen in FIGS. 7A and 7B a band was detected using both the unmethylated blockers and the methylated blockers. If MSP had been used this particular sample would have produced a false positive band as the priming site for the second MSP PCR primer would be unmethylated hence the primer would not bind.

Using the methylated INA blockers all results agreed with the results obtained by conventional bisulphite sequencing.

Clinical Testing Results

Figure 8:
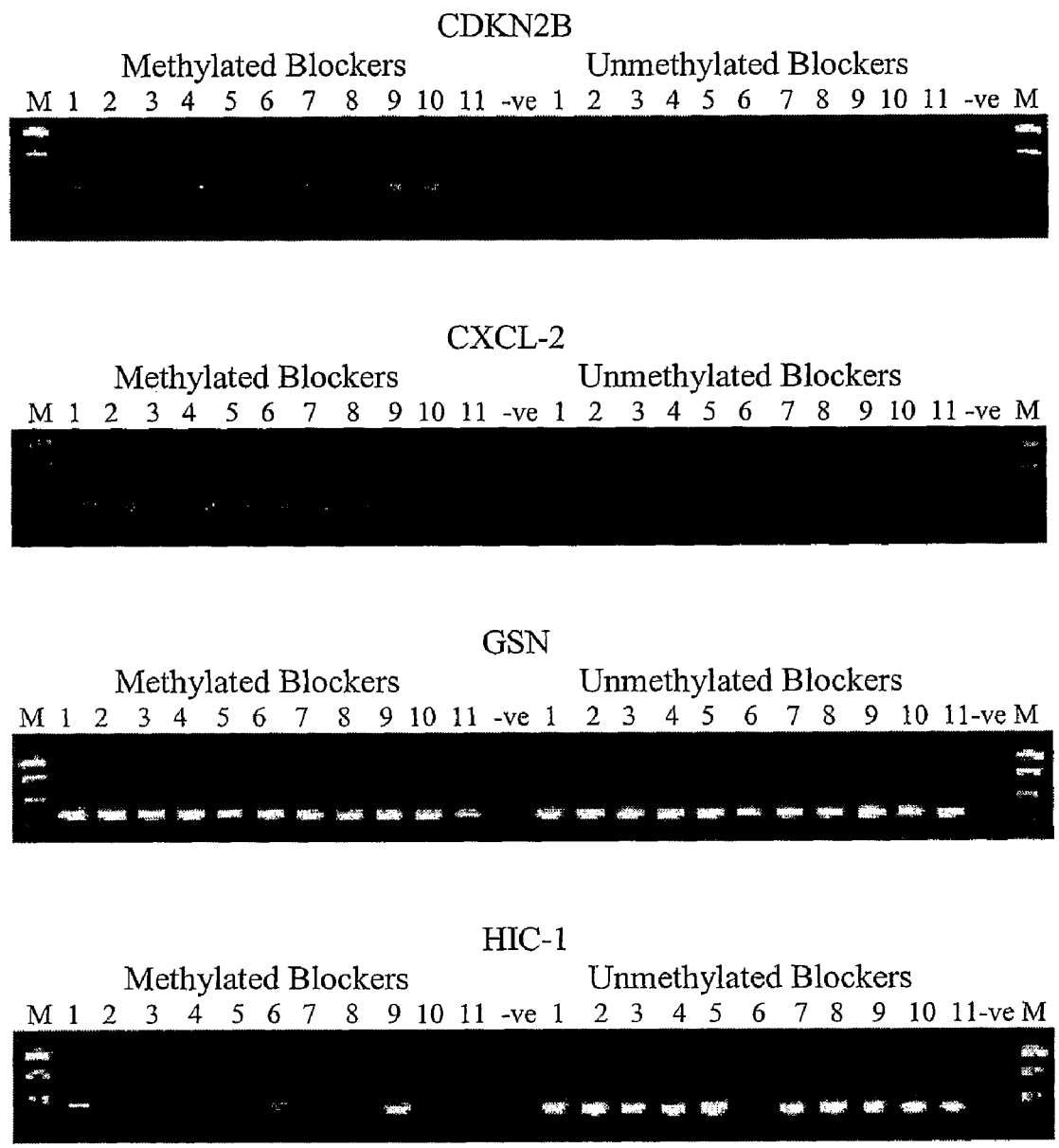
FIG. 8 shows amplification results and inferred methylation status of four genomic regions near to the CDKN2B, CXCL-2, GSN and HIC-1 genes using blockers and PCR primers applied to the eleven genomic DNA samples described in Table 2. The results are of the use of blockers and PCR primers applied to eleven genomic DNA samples described in Table 3, and reveals the amplification products from human genomic regions in the vicinity of the CDKN2B, CXCL-2, GSN and HIC-1 loci.

FIG. 8 and Table 3 show the results of blocker experiments on four genomic regions (CDKN2B, CXCL-2, GSN and HIC-1) from eleven different samples of cell lines or clinical samples. The blockers used and experimental protocol were as follows:

PCR premixes were prepared as follows for each gene region of interest:

| | Unmethylated mixes | Methylated mixes |
|---|---|---|
| X2 Master mix (Promega) | 12.5 μl | 12.5 μl |
| 100 ng/μl PCR#1 | 1 μl | 1 μl |
| 100 ng/μl PCR#2 | 1 μl | 1 μl |
| 200 ng/μl Blocker#1 | 1.5 μl (U) | 1.5 μl (M) |
| 200 ng/μl Blocker#2 | 1.5 μl (U) | 1.5 μl (M) |
| 200 ng/μl Blocker#3 | 1.5 μl (U) | 1.5 μl (M) |
| 200 ng/μl Blocker#4 | 1.5 μl (U) | 1.5 μl (M) |
| Water | 3.5 μl | 3.5 μl |

Two rounds of PCR amplification were performed in a Hybaid PX2 thermocycler according to the principles described in FIG. 1. One μl of bisulphite treated genomic DNA was added to each of the 1$^{st}$ round PCR reaction tubes. The PCR was carried out as follows.

| 95° C. | 3 minutes | 1 cycle |
|---|---|---|
| 95° C. | 1 minute | |
| 50° C. | 2 minutes | 30 cycles |
| 72° C. | 2 minutes | |
| 72° C. | 10 minutes | 1 cycle |

After the 1$^{st}$ round PCR was complete, 1 μl of the 1$^{st}$ round PCR reaction mixture was transfered to the second round amplification tubes and the above PCR program repeated.

Ten μl of the PCR reaction mix was then resolved on a 2% agarose gel.

TABLE 3

| Lane | Sample | Source | Methylation | | | |
|---|---|---|---|---|---|---|
| | | | CDKN2B | CXCL-2 | GSN | HIC-1 |
| 1-CL | Du145 | prostate cancer | ND | ND | ND | ND |
| 2-CL | BL13 | bladder cancer | no | No | mixed | yes |
| 3-CL | MRC-5 | fibroblast - normal | ND | ND | ND | ND |
| 4-CL | T47D2 | breast cancer | ND | ND | ND | ND |
| 5-CL | HeLa | cervix cancer | No | No | ND | yes |
| 6-CL | SMC | muscle - normal | ND | ND | ND | ND |
| 7-CL | MCF-7 | breast cancer | No | No | mixed | ND |
| 8-CL | LNCaP | prostate cancer | No | No | mixed | yes |
| 9-Pa | granulocytes | blood - Leukemia | No | No | No | No |
| 10-Pa | T-cells | blood - Leukemia | No | No | mixed | No |
| 11-CL | THP-1 | blood - Leukemia | ND | ND | ND | ND |

CL - Denotes the material was derived from a cell line.
Pa - Denotes cells were obtained from a patient
ND - Not Determined
No - No methylation detected by direct sequencing of the PCR product
mixed - Not all CpG sites methylated or methylation confined to one region within the amplicon
yes - Methylation detected by direct sequencing of the amplicon.

Genomic regions CDKN2B and CXCL-2 were found to be unmethylated in almost all samples except for a small amount of methylation revealed as a weak band in granulocytes. The results were confirmed by independent amplification on selected samples followed by direct sequencing of the PCR products. Direct DNA sequencing revealed no methylation in any of the CDKN2B or CXCL-2 PCR fragments. The sensitivity of direct sequencing is such that unless more that 10% of the amplified material are methylated the sequence will read as unmethylated. Thus the presence of the weak band for CXCL-2 in the granulocyte sample is indicative of a very low level of methylation in this sample (<10%) detected by the blocker assay.

In all samples sequenced for the GSN genomic region, mixed methylation patterns were observed agreeing with the results of the blocker assays. The methylation pattern of this genomic region varied throughout the length of the PCR amplicon and in many cases not all CpG dinucleotides were methylated or a mixture of unmethylated and methylated sequences were observed at individual CpG sites.

Methylation of the Hypermethylated In Cancer (HIC-1) gene was observed for BL13, Hela and LNCaP cell lines with all CpG sites showing 100% methylation. Interestingly, the normal SMC (sample 6) cell line was the only cell line to show no methylation of the HIC-1 gene. The granulocytes and T-cells (samples 9 and 10) from a patient in remission for leukemia showed mixed methylation by the blocker assay and although the PCR amplicons for the vast majority appeared unmethylated this again may be due to the lack of sensitivity of the direct sequencing approach.

It can be seen from the results that the blocker assay according to the present invention is a powerful tool to detect methylation patterns of various regions of the human genome.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method for detecting the methylation status of a target region of a nucleic acid molecule comprising:

treating the nucleic acid molecule with an agent which modifies cytosine bases but does not modify 5-methylcytosine bases under conditions to form a modified nucleic acid template;

providing to an amplification reaction a first amplification blocker comprising an intercalating nucleic acid (INA) containing two or more internal intercalating pseudonucleotides, the first blocker being complementary to the unmethylated target region on a first strand of the modified nucleic acid template;

providing to the amplification reaction a second amplification blocker comprising an intercalating nucleic acid (INA) containing two or more internal intercalating pseudonucleotides, the second blocker being complementary to a second region on a second strand complementary to the first strand of the modified nucleic acid template, the second region being downstream of the target region of the first strand of the modified nucleic acid template;

providing a first primer complementary to a nucleic acid region upstream from the target region on the first strand of the modified nucleic acid template;

providing a second primer complementary to a nucleic acid region upstream from the second blocker region on the second strand complementary to the first strand of the modified nucleic acid template; and carrying out an amplification reaction on the modified nucleic acid template, wherein if the target region is methylated there will be an amplification product and if the target region is unmethylated there will be no amplification product;

wherein the internal intercalating pseudonucleotides are essentially planar polyaromatic or heteropolyaromatic compounds that are capable of co-stacking with nucleobases in a nucleic acid duplex and are not peptide nucleic acids and wherein the internal intercalating pseudonucleotides prevent extension of at least one of the blockers by a polymerase when said at least one of the blockers is bound to a nucleic acid template.

2. The method according to claim 1, further comprising:

providing third and fourth amplification blockers comprising an intercalating nucleic acid (INA) containing two or more internal intercalating pseudonucleotides to the amplification reaction, the third and fourth blockers being complementary to regions internal to the first and second blocker regions; and providing third and fourth primers complementary to regions external to the third and fourth blocker regions and internal to the first and second primer regions.

3. The method according to claim 1, further comprising:

providing one or more additional amplification blockers comprising an intercalating nucleic acid (INA) containing two or more internal intercalating pseudonucleotides directed to one or more additional regions on the nucleic acid molecule.

4. The method according to claim 3, wherein the one or more additional regions on the nucleic acid molecule correspond to one or more additional regions on the modified nucleic acid template.

5. The method according to claim 1, further comprising:

providing one or more additional amplification blockers comprising an intercalating nucleic acid (INA) containing two or more internal intercalating pseudonucleotides directed to the first strand of the modified nucleic acid template or its complementary second strand complementary to regions between the first and second primer regions.

6. The method according to claim 1 wherein the target region-comprises cytosine (C) flanked 3' by a guanine (G).

7. The method according to claim 1, wherein the modifying agent is selected from the group consisting of bisulfite, acetate and citrate.

8. The method according to claim 7 wherein the modifying agent is sodium bisulfite.

9. The method according to claim 1 wherein the nucleic acid molecule is DNA.

10. The method according to claim 1 wherein the INA is about 15 to 50 nucleotides or nucleotide analogues in length having 2 to 6 internal intercalating pseudonucleotides.

11. The method according to claim 10 wherein the INA is about 18 to 35 nucleotides or nucleotide analogues in length having 2 to 6 internal intercalating pseudonucleotides.

12. The method according to claim 1 wherein the internal intercalating pseudonucleotides are situated 2 or more bases from the 3' or 5' end of a blocker.

13. The method according to claim 1 wherein the INA contains no intercalating pseudonucleotides at either the 3' or 5' end of a blocker.

14. The method according to claim 1 wherein the internal intercalating pseudonucleotide is selected from phosphoramidites of 1-(4,4'-dimethoxytriphenylmethyloxy)-3-pyrenemethyloxy-2-propanol.

15. The method according to claim 14 wherein the internal intercalating pseudonucleotide is selected from the phosphoramidite of (S)-1-(4,4'-dimethoxytriphenylmethyloxy)-3-pyrenemethyloxy -2-propanol or the phosphoramidite of (R)-1-(4,4'-dimethoxytriphenylmethyloxy) -3-pyrenemethyloxy-2-propanol.

16. The method according to claim 15 wherein the internal intercalating pseudonucleotide is the phosphoramidite of (S)-1-(4,4'-dimethoxytriphenylmethyloxy)-3-pyrenemethyloxy-2-propanol.

17. The method according to claim 1 wherein the amplification assay is PCR.

18. A method for detecting the methylation status of a target region of a nucleic acid molecule comprising:
treating the nucleic acid molecule with an agent which modifies cytosine bases but does not modify 5-methylcytosine bases under conditions to form a modified nucleic acid template;
providing to an amplification reaction a first amplification blocker comprising an intercalating nucleic acid (INA) containing two or more internal intercalating pseudonucleotides, the first blocker being complementary to the methylated target region on a first strand of the modified nucleic acid template;
providing to the amplification reaction a second amplification blocker comprising an intercalating nucleic acid (INA) containing two or more internal intercalating pseudonucleotides, the second blocker being complementary to a second region on a second strand complementary to the first strand of the modified nucleic acid template, the second region being downstream of the target region of the first strand of the modified nucleic acid template;
providing a first primer complementary to a nucleic acid region upstream from the target region on the first strand of the modified nucleic acid template;
providing a second primer complementary to a nucleic acid region upstream from the second blocker region on the second strand complementary to the first strand of the modified nucleic acid template; and
carrying out an amplification reaction on the modified nucleic acid template, wherein if the target region is unmethylated there will be an amplification product and if the target region is methylated there will be no amplification product;
wherein the internal intercalating pseudonucleotides are essentially planar polyaromatic or heteropolyaromatic compounds that are capable of co-stacking with nucleobases in a nucleic acid duplex and are not peptide nucleic acids and wherein the internal intercalating pseudonucleotides prevent extension of at least one of the blockers by a polymerase when said at least one of the blockers is bound to a nucleic acid template.

19. The method according to claim 18 further comprising:
providing third and fourth amplification blockers comprising an intercalating nucleic acid (INA) containing two or more internal intercalating pseudonucleotides to the amplification reaction, the third and fourth blockers being complementary to regions internal to the first and second blocker regions; and
providing third and fourth primers complementary to regions external to the third and fourth blocker regions and internal to the first and second primer regions.

20. The method according to claim 18 further comprising:
providing one or more additional amplification blockers comprising an intercalating nucleic acid (INA) containing two or more internal intercalating pseudonucleotides directed to one or more additional regions on the nucleic acid molecule.

21. The method according to claim 20 wherein the one or more additional regions on the nucleic acid molecule correspond to one or more additional regions on the modified nucleic acid template.

22. The method according to claim 18 further comprising:
providing one or more additional amplification blockers comprising an intercalating nucleic acid (INA) containing two or more internal intercalating pseudonucleotides directed to the first strand of the modified nucleic acid template or its complementary second strand complementary to regions between the first and second primer regions.

23. The method according to claim 18 wherein the target region comprises cytosine (C) flanked 3' by a guanine (G).

24. The method according to claim 18 wherein the modifying agent is selected from the group consisting of bisulfite, acetate and citrate.

25. The method according to claim 24 wherein the modifying agent is sodium bisulfite.

26. The method according to claim 18 wherein the nucleic acid molecule is DNA.

27. The method according to claim 18 wherein the INA is about 15 to 50 nucleotides or nucleotide analogues in length having 2 to 6 internal intercalating pseudonucleotides.

28. The method according to claim 27 wherein the INA is about 18 to 35 nucleotides or nucleotide analogues in length having 2 to 6 internal intercalating pseudonucleotides.

29. The method according to claim 18 wherein the internal intercalating pseudonucleotides are situated 2 or more bases from the 3' or 5' end of a blocker.

30. The method according to claim 18 wherein the INA contains no intercalating pseudonucleotides at either the 3' or 5' end of a blocker.

31. The method according to claim 18 wherein the internal intercalating pseudonucleotide is selected from phosphoramidites of 1-(4,4'-dimethoxytriphenylmethyloxy)-3-pyrenemethyloxy-2-propanol.

32. The method according to claim 31 wherein the internal intercalating pseudonucleotide is selected from the phosphoramidite of (S)-1-(4,4'-dimethoxytriphenylmethyloxy)-3-pyrenemethyloxy -2-propanol or the phosphoramidite of (R)-1-(4,4'-dimethoxytriphenylmethyloxy) -3-pyrenemethyloxy-2-propanol.

33. The method according to claim 32 wherein the internal intercalating pseudonucleotide is the phosphoramidite of (S)-1-(4,4'-dimethoxytriphenylmethyloxy)-3-pyrenemethyloxy-2-propanol.

34. The method according to claim 18 wherein the amplification assay is polymerase chain reaction.

35. A method for detecting a conversion status of a target region of a nucleic acid molecule comprising:
   treating the nucleic acid molecule with an agent which modifies cytosine bases but does not modify 5-methylcytosine bases under conditions to form a modified nucleic acid template;
   providing to an amplification reaction a first amplification blocker comprising an intercalating nucleic acid (INA) containing two or more internal intercalating pseudonucleotides, the first blocker being complementary to the unconverted target region on a first strand of the modified nucleic acid template;
   providing to the amplification reaction a second amplification blocker comprising an intercalating nucleic acid (INA) containing two or more internal intercalating pseudonucleotides, the second blocker being complementary to a second region on a second strand complementary to the first strand of the modified nucleic acid template, the second region being downstream of the target region of the first strand of the modified nucleic acid template;
   providing a first primer complementary to a nucleic acid region upstream from the target region on the first strand of the modified nucleic acid template;
   providing a second primer complementary to a nucleic acid region upstream from the second blocker region on the second strand complementary to the first strand of the modified nucleic acid template; and
   carrying out an amplification reaction on the modified nucleic acid template, wherein if the target region is converted there will be an amplification product and if the target region is unconverted there will be no amplification product;
   wherein the internal intercalating pseudonucleotides are essentially planar polyaromatic or heteropolyaromatic compounds that are capable of co-stacking with nucleobases in a nucleic acid duplex and are not peptide nucleic acids and wherein the internal intercalating pseudonucleotides prevent extension of at least one of the blockers by a polymerase when said at least one of the blockers is bound to a nucleic acid template.

36. The method according to claim 35 wherein the target region comprises cytosine (C) flanked 3' by a guanine (G).

37. The method according to claim 35 wherein the modifying agent is selected from the group consisting of bisulfite, acetate and citrate.

38. The method according to claim 37 wherein the modifying agent is sodium bisulfite.

39. The method according to claim 35 wherein the nucleic acid molecule is DNA.

40. The method according to claim 35 wherein the INA is about 15 to 50 nucleotides or nucleotide analogues in length having 2 to 6 internal intercalating pseudonucleotides.

41. The method according to claim 40 wherein the INA is about 18 to 35 nucleotides or nucleotide analogues in length having 2 to 6 internal intercalating pseudonucleotides.

42. The method according to claim 35 wherein the internal intercalating pseudonucleotides are situated 2 or more bases from the 3' or 5' end of a blocker.

43. The method according to claim 35 wherein the INA contains no intercalating pseudonucleotides at either the 3' or 5' end of a blocker.

44. The method according to claim 35 wherein the internal intercalating pseudonucleotide is selected from phosphoramidites of 1-(4,4'-dimethoxytriphenylmethyloxy)-3-pyrenemethyloxy-2-propanol.

45. The method according to claim 44 wherein the internal intercalating pseudonucleotide is selected from the phosphoramidite of (S)-1-(4,4'-dimethoxytriphenylmethyloxy)-3-pyrenemethyloxy -2-propanol or the phosphoramidite of (R)-1-(4,4'-dimethoxytriphenylmethyloxy) -3-pyrenemethyloxy-2-propanol.

46. The method according to claim 45 wherein the internal intercalating pseudonucleotide is the phosphoramidite of (S)-1-(4,4'-dimethoxytriphenylmethyloxy)-3-pyrenemethyloxy-2propanol.

47. The method according to claim 35 wherein the amplification assay is polymerase chain reaction.

48. A method for detecting a conversion status of a target region of a nucleic acid molecule comprising:
   treating the nucleic acid molecule with an agent which modifies cytosine bases but does not modify 5-methylcytosine bases under conditions to form a modified nucleic acid template;
   providing to an amplification reaction a first amplification blocker comprising an intercalating nucleic acid (INA) containing two or more internal intercalating pseudonucleotides, the first blocker being complementary to the converted target region on a first strand of the modified nucleic acid template;
   providing to the amplification reaction a second amplification blocker comprising an intercalating nucleic acid (INA) containing two or more internal intercalating pseudonucleotides, the second blocker being complementary to a second region on a second strand complementary to the first strand of the modified nucleic acid template, the second region being downstream of the target region of the first strand of the modified nucleic acid template;
   providing a first primer complementary to a nucleic acid region upstream from the target region on the first strand of the modified nucleic acid template;
   providing a second primer complementary to a nucleic acid region upstream from the second blocker region on the second strand complementary to the first strand of the modified nucleic acid template; and
   carrying out an amplification reaction on the modified nucleic acid template, wherein if the target region is unconverted there will be an amplification product and if the target region is converted there will be no amplification product;
   wherein the internal intercalating pseudonucleotides are essentially planar polyaromatic or heteropolyaromatic compounds that are capable of co-stacking with nucleobases in a nucleic acid duplex and are not peptide nucleic acids and wherein the internal intercalating pseudonucleotides prevent extension of at least one of the blockers by a polymerase when said at least one of the blockers is bound to a nucleic acid template.

49. The method according to claim 48 wherein the target region comprises cytosine (C) flanked 3' by a guanine (G).

50. The method according to claim 48 wherein the modifying agent is selected from the group consisting of bisulfite, acetate and citrate.

51. The method according to claim 50 wherein the modifying agent is sodium bisulfite.

52. The method according to claim 48 wherein the nucleic acid molecule is DNA.

53. The method according to claim 48 wherein the INA is about 15 to 50 nucleotides or nucleotide analogues in length having 2 to 6 internal intercalating pseudonucleotides.

54. The method according to claim 53 wherein the INA is about 18 to 35 nucleotides or nucleotide analogues in length having 2 to 6 internal intercalating pseudonucleotides.

55. The method according to claim 48 wherein the internal intercalating pseudonucleotides are situated 2 or more bases from the 3' or 5' end of a blocker.

56. The method according to claim 48 wherein the INA contains no intercalating pseudonucleotides at either the 3' or 5' end of a blocker.

57. The method according to claim 48 wherein the internal intercalating pseudonucleotide is selected from phosphoramidites of 1-(4,4'-dimethoxytriphenylmethyloxy)-3-pyrenemethyloxy-2-propanol.

58. The method according to claim 57 wherein the internal intercalating pseudonucleotide is selected from the phosphoramidite of (S)-1-(4,4'-dimethoxytriphenylmethyloxy)-3-pyrenemethyloxy -2-propanol or the phosphoramidite of (R)-1-(4,4'-dimethoxytriphenylmethyloxy) -3-pyrenemethyloxy-2-propanol.

59. The method according to claim 58 wherein the internal intercalating pseudonucleotide is the phosphoramidite of (S)-1-(4,4'-dimethoxytriphenylmethyloxy)-3-pyrenemethyloxy-2-propanol.

60. The method according to claim 48 wherein the amplification assay is polymerase chain reaction.

61. A method for detecting a status of a target region of a nucleic acid molecule comprising:
    treating the nucleic acid molecule with an agent which modifies cytosine bases but does not modify 5-methylcytosine bases under conditions to form a modified nucleic acid template;
    providing to an amplification reaction a first amplification blocker comprising an intercalating nucleic acid (INA) containing two or more internal intercalating pseudonucleotides, the first blocker being complementary to a target region on a first strand of the modified nucleic acid template having a methylation status indicative of the presence of a disease state;
    providing to the amplification reaction a second amplification blocker comprising an intercalating nucleic acid (INA) containing two or more internal intercalating pseudonucleotides, the second blocker being complementary to a second region on a second strand complementary to the first strand of the modified nucleic acid template, the second region being downstream of the target region of the first strand of the modified nucleic acid template;
    providing a first primer complementary to a nucleic acid region upstream from the target region on the first strand of the modified nucleic acid template;
    providing a second primer complementary to a nucleic acid region upstream from the second blocker region on the second strand complementary to the first strand of the modified nucleic acid template; and
    carrying out an amplification reaction on the modified nucleic acid template, wherein if the target region has a methylation status which is not indicative of a disease state there will be an amplification product and if the target region has a methylation status which is indicative of a disease state there will be no amplification product;
    wherein the internal intercalating pseudonucleotides are essentially planar polyaromatic or heteropolyaromatic compounds that are capable of co-stacking with nucleobases in a nucleic acid duplex and are not peptide nucleic acids and wherein the internal intercalating pseudonucleotides prevent extension of at least one of the blockers by a polymerase when said at least one of the blockers is bound to a nucleic acid template.

62. The method according to claim 61 wherein the INA is about 15 to 50 nucleotides or nucleotide analogues in length having 2 to 6 internal intercalating pseudonucleotides.

63. The method according to claim 62 wherein the INA is about 18 to 35 nucleotides or nucleotide analogues in length having 2 to 6 internal intercalating pseudonucleotides.

64. The method according to claim 61 wherein the internal intercalating pseudonucleotides are situated 2 or more bases from the 3' or 5' end of a blocker.

65. The method according to claim 61 wherein the INA contains no intercalating pseudonucleotides at either the 3' or 5' end of a blocker.

66. The method according to claim 61 wherein the internal intercalating pseudonucleotide is selected from phosphoramidites of 1-(4,4'-dimethoxytriphenylmethyloxy)-3-pyrenemethyloxy-2-propanol.

67. The method according to claim 66 wherein the internal intercalating pseudonucleotide is selected from the phosphoramidite of (S)-1-(4,4'-dimethoxytriphenylmethyloxy) -3-pyrenemethyloxy-2-propanol or the phosphoramidite of (R)-1-(4,4'-dimethoxytriphenylmethyloxy) -3-pyrenemethyloxy-2-propanol.

68. The method according to claim 67 wherein the internal intercalating pseudonucleotide is the phosphoramidite of (S)-1-(4,4'-dimethoxytriphenylmethyloxy)-3-pyrenemethyloxy -2-propanol.

69. A method for detecting a status of a target region of a nucleic acid molecule comprising:
    treating the nucleic acid molecule with an agent which modifies cytosine bases but does not modify 5-methylcytosine bases under conditions to form a modified nucleic acid template;
    providing to an amplification reaction a first amplification blocker comprising an intercalating nucleic acid (INA) containing two or more internal intercalating pseudonucleotides, the first blocker being complementary to a target region on a first strand of the modified nucleic acid template having a methylation status which is not indicative of a disease state;
    providing to the amplification reaction a second amplification blocker comprising an intercalating nucleic acid (INA) containing two or more internal intercalating pseudonucleotides, the second blocker being complementary to a region on the complementary second strand downstream of the first strand of the modified nucleic acid template;
    providing a first primer complementary to a nucleic acid region upstream from the target region on the first strand of the modified nucleic acid template;
    providing a second primer complementary to a nucleic acid region upstream from the second blocker region on the second strand complementary to the first strand of the modified nucleic acid template;
    carrying out an amplification reaction on the modified nucleic acid template, wherein if the target region has a methylation status indicative of a disease state there will be an amplification product and if the target region has a methylation status which is not indicative of a disease state there will be no amplification product;
    wherein the internal intercalating pseudonucleotides are being planar polyaromatic or heteropolyaromatic compounds that are capable of co-stacking with nucleobases in a nucleic acid duplex and are not peptide nucleic acids and wherein the internal intercalating pseudonucleotides prevent extension of at least one of the blockers by a polymerase when said at least one of the blockers is bound to a nucleic acid template.

70. The method according to claim 69 wherein the INA is about 15 to 50 nucleotides or nucleotide analogues in length having 2 to 6 internal intercalating pseudonucleotides.

71. The method according to claim 70 wherein the INA is about 18 to 35 nucleotides or nucleotide analogues in length having 2 to 6 internal intercalating pseudonucleotides.

72. The method according to claim 69 wherein the internal intercalating pseudonucleotides are situated 2 or more bases from the 3' or 5' end of a blocker.

73. The method according to claim 69 wherein the INA contains no intercalating pseudonucleotides at either the 3' or 5' end of a blocker.

74. The method according to claim 69 wherein the internal intercalating pseudonucleotide is selected from phosphoramidites of 1-(4,4'-dimethoxytriphenylmethyloxy)-3-pyrenemethyloxy-2-propanol.

75. The method according to claim 74 wherein the internal intercalating pseudonucleotide is selected from the phosphoramidite of (S)-1-(4,4'-dimethoxytriphenylmethyloxy)-3-pyrenemethyloxy-2-propanol or the phosphoramidite of (R)-1-(4, 4'-dimethoxytriphenylmethyloxy)-3-pyrenemethyloxy-2-propanol.

76. The method according to claim 75 wherein the internal intercalating pseudonucleotide is the phosphoramidite of (S)-1-(4,4-dimethoxytriphenylmethyloxy)-3-pyrenemethyloxy-2-propanol.

77. A method for detecting the methylation status of a target region of a nucleic acid molecule comprising:
   treating the nucleic acid molecule with an agent which modifies cytosine bases but does not modify 5-methyl-cytosine bases under conditions to form a modified nucleic acid template;
   providing to an amplification reaction a first amplification blocker comprising an intercalating nucleic acid (INA) containing two or more internal intercalating pseudonucleotides, the first blocker being complementary to the unmethylated target region on a first strand of the modified nucleic acid template;
   providing to the amplification reaction a second amplification blocker comprising an intercalating nucleic acid (INA) containing two or more internal intercalating pseudonucleotides, the second blocker being complementary to a second region on a second strand complementary to the first strand of the modified nucleic acid template, the second region being downstream of the target region of the first strand of the modified nucleic acid template;
   providing a first primer complementary to a nucleic acid region upstream from the target region on the first strand of the modified nucleic acid template;
   providing a second primer complementary to a nucleic acid region upstream from the second blocker region on the second strand complementary to the first strand of the modified nucleic acid template;
   providing third and fourth amplification blockers comprising an intercalating nucleic acid (INA) containing two or more internal intercalating pseudonucleotides to the amplification reaction, the third and fourth blockers being complementary to regions internal to the first and second blocker regions; and
   providing third and fourth primers complementary to regions external to the third and fourth blocker regions and internal to the first and second primer regions;
   carrying out an amplification reaction on the modified nucleic acid template, wherein if the target region is methylated there will be an amplification product and if the target region is unmethylated there will be no amplification product;
   wherein the internal intercalating pseudonucleotides are essentially planar polyaromatic or heteropolyaromatic compounds that are capable of co-stacking with nucleobases in a nucleic acid duplex and are not peptide nucleic acids.

78. A method for detecting the methylation status of a target region of a nucleic acid molecule comprising:
   treating the nucleic acid molecule with an agent which modifies cytosine bases but does not modify 5-methyl-cytosine bases under conditions to form a modified nucleic acid template;
   providing to an amplification reaction a first amplification blocker comprising an intercalating nucleic acid (INA) containing two or more internal intercalating pseudonucleotides, the first blocker being complementary to the methylated target region on a first strand of the modified nucleic acid template;
   providing to the amplification reaction a second amplification blocker comprising an intercalating nucleic acid (INA) containing two or more internal intercalating pseudonucleotides, the second blocker being complementary to a second region on a second strand complementary to the first strand of the modified nucleic acid template, the second region being downstream of the target region of the first strand of the modified nucleic acid template;
   providing a first primer complementary to a nucleic acid region upstream from the target region on the first strand of the modified nucleic acid template;
   providing a second primer complementary to a nucleic acid region upstream from the second blocker region on the second strand complementary to the first strand of the modified nucleic acid template;
   providing third and fourth amplification blockers comprising an intercalating nucleic acid (INA) containing two or more internal intercalating pseudonucleotides to the amplification reaction, the third and fourth blockers being complementary to regions internal to the first and second blocker regions;
   providing third and fourth primers complementary to regions external to the third and fourth blocker regions and internal to the first and second primer regions; and
   carrying out an amplification reaction on the modified nucleic acid template, wherein if the target region is unmethylated there will be an amplification product and if the target region is methylated there will be no amplification product;
   wherein the internal intercalating pseudonucleotides are essentially planar polyaromatic or heteropolyaromatic compounds that are capable of co-stacking with nucleobases in a nucleic acid duplex and are not peptide nucleic acids.

* * * * *